US010507307B2

(12) United States Patent
Gottlieb et al.

(10) Patent No.: US 10,507,307 B2
(45) Date of Patent: Dec. 17, 2019

(54) GUIDEWIRE FOR CATHETER INSERTION

(71) Applicant: Horizon Patents, LLC, Fairfax Station, VA (US)

(72) Inventors: Mark M. Gottlieb, Fairfax Station, VA (US); James B. Solomon, Vienna, VA (US)

(73) Assignee: Horizon Patents, LLC, Fairfax Station, VA (US)

( * ) Notice: Subject to any disclaimer, the term of this patent is extended or adjusted under 35 U.S.C. 154(b) by 0 days.

(21) Appl. No.: 16/142,180

(22) Filed: Sep. 26, 2018

(65) Prior Publication Data

US 2019/0262587 A1    Aug. 29, 2019

Related U.S. Application Data

(60) Provisional application No. 62/635,008, filed on Feb. 26, 2018.

(51) Int. Cl.
*A61B 5/00* (2006.01)
*A61M 25/09* (2006.01)

(52) U.S. Cl.
CPC ...... *A61M 25/09* (2013.01); *A61M 25/09041* (2013.01); *A61M 2025/09133* (2013.01);
(Continued)

(58) Field of Classification Search
CPC ............ A61M 25/09; A61M 25/09041; A61M 2205/6081; A61M 2025/09141; A61M 2025/09133
(Continued)

(56) References Cited

U.S. PATENT DOCUMENTS 4,545,390 A    10/1985   Leary
5,059,183 A    10/1991   Semrad
(Continued)

FOREIGN PATENT DOCUMENTS

EP           0495299 A1     7/1992
EP           0 812 599 B1   8/2002
WO     WO1998056687 A1    12/1998

OTHER PUBLICATIONS

International Search Report and Written Opinion dated Apr. 30, 2019, in International Application No. PCT/US19/19107.

*Primary Examiner* — Max F Hindenburg
(74) *Attorney, Agent, or Firm* — Oblon, McClelland, Maier & Neustadt, L.L.P.

(57) ABSTRACT

The present invention is directed to a guidewire configured to reduce the incidence of medical accidents when using guidewires including, but not limited to, the incidence of guidewires accidentally being pushed completely into a patient through a needle in the patient, guidewires accidently being left inside patients after the placement of central venous (and other) catheters, and guidewires accidently being left inside patients after removal of the catheter (at the end of an operation of other medical procedure). In particular, an intermediary portion (either in the form of a new shape (referred to herein as "an obstruction portion") or an alternate (e.g., more flexible) material) of the guidewire inhibits further advancement into the needle with pushing motion. (The intermediary portion can be implemented as an additional portion connected between the patient-side portion and the doctor-side portion of the guidewire as well.)

34 Claims, 30 Drawing Sheets

(52) U.S. Cl.
CPC .............. *A61M 2025/09141* (2013.01); *A61M 2205/6081* (2013.01)

(58) Field of Classification Search
USPC ........................................................ 600/585
See application file for complete search history.

(56) References Cited

U.S. PATENT DOCUMENTS

| | | | | |
|---|---|---|---|---|
| 5,411,033 | A | 5/1995 | Viera | |
| 5,441,055 | A * | 8/1995 | Ales | A61M 25/0905 600/434 |
| 5,497,782 | A | 3/1996 | Fugoso | |
| 5,546,958 | A * | 8/1996 | Thorud | A61M 25/0905 600/434 |
| 5,605,163 | A * | 2/1997 | Hani | A61M 25/0905 600/434 |
| 5,617,875 | A * | 4/1997 | Schwager | A61M 25/0905 600/585 |
| 5,664,580 | A | 9/1997 | Erickson | |
| 5,730,150 | A | 3/1998 | Peppel | |
| 7,153,277 | B2 * | 12/2006 | Skujins | A61M 25/09 600/585 |
| 7,182,735 | B2 * | 2/2007 | Shireman | A61M 25/09 600/585 |
| 7,691,081 | B2 | 4/2010 | Crossman | |
| 8,376,961 | B2 * | 2/2013 | Layman | A61M 25/0068 600/434 |
| 8,454,536 | B2 | 6/2013 | Raulerson | |
| 8,968,215 | B2 * | 3/2015 | Murayama | A61M 25/09 600/585 |
| 9,192,742 | B2 * | 11/2015 | Pursley | A61M 25/0009 |
| 9,492,642 | B2 * | 11/2016 | Miyata | A61M 25/09 |
| 9,504,806 | B2 | 11/2016 | Gallacher | |
| 9,968,762 | B2 * | 5/2018 | Green | A61M 25/09 |
| 10,039,903 | B2 * | 8/2018 | Kay | A61M 25/09 |
| 2003/0171642 | A1 | 9/2003 | Schock | |
| 2007/0021685 | A1 | 1/2007 | Oepen | |
| 2015/0038943 | A1 | 2/2015 | Warring | |

* cited by examiner

GUIDEWIRE FOR CATHETER INSERTION

CROSS-REFERENCE TO CO-PENDING APPLICATION

The present application claims priority to U.S. Provisional Patent Application No. 62/635,008 filed Feb. 26, 2018, the contents of which are incorporated herein by reference.

FIELD OF INVENTION

The present invention is directed to a guidewire for use with a catheter, and, in one embodiment, to a guidewire for use with a central venous catheter (CVC) which are used together in a medical procedure or operation.

DISCUSSION OF THE BACKGROUND

A "central venous catheter" (CVC), also known as a "central line," "central venous line," or "central venous access catheter," is a catheter placed into a large vein. Catheters, such as the known 3 lumen catheter of FIG. 1, can be placed in veins in the neck (internal jugular vein), chest (subclavian vein or axillary vein), groin (femoral vein), or through veins in the arms (also known as a peripherally inserted central catheters (PICC) line). It is used to administer medication or fluids that are unable to be taken by mouth or would harm a smaller peripheral vein, obtain blood tests (specifically the "central venous oxygen saturation"), and to measure central venous pressure. FIGS. 2A and 2B illustrate catheters having been inserted into patients.

More than 50 million surgical procedures were performed in the United States. As part of some of those procedures, central venous catheters are inserted into patients. Before a catheter is placed into a patient, a guidewire must be inserted in the blood vessel to act as a guide for the catheter. The guidewire has become an integral part of a growing number of medical procedures with its use steadily increasing and expanding into more and more medical specialties, particularly as non-invasive procedures have been developed.

A guidewire is a thin, flexible, medical wire inserted into the body to guide a larger instrument, such as a catheter, central venous line, or feeding tube. The materials used to make guidewires have varied over the years but today they primarily consist of stainless steel and Nitinol (nickel titanium). Not all of a guidewire is placed into a patient as the guidewire must be retrievable after insertion of the catheter. As used herein, the phrase "the patient-side of the guidewire" will be used to refer to at least the end of the guidewire that is inserted into the patient.

The placement of a central venous catheter is frequently necessary for patients in the operating room or the intensive care unit. In fact, millions were placed last year in the United States alone. These are large IVs that are typically placed in the neck, shoulder, or groin. The blood vessel is penetrated with a hollow needle and a guidewire is then advanced through the needle into the vessel. In some embodiments, guidewire diameters range in size from 0.012" to 0.063", but smaller or larger guidewires can be used depending on the operation. In known configurations, a matching needle and catheter used with its corresponding guidewire has a hole with an inner diameter that is 10-30% larger than the diameter of the corresponding guidewire. The needle is removed, leaving the wire in place, and the catheter is advanced over exposed or doctor end of the guidewire until the first part of the wire extends outside the back of the catheter. (The term "doctor" as used herein is intended to mean both doctors and any medical professionals working under the supervision of a doctor (e.g., an intern, resident or surgical nurse).) Then, while holding the wire in place so that it does not move, the catheter is advanced into proper position within the vessel. Once the catheter is in place the wire is removed and discarded.

The most common complications of central venous catheters are infection and damage to surrounding structures. A less common but more serious complication is the accidental failure to remove the guidewire after placement and at times after the operation is complete—leaving the guidewire fully retained within the body. Despite the rare occurrence (approx. 1 per 3,000 placements), these retained guidewires cause significant potential harm to the patient including more surgeries, more lengthy hospital stays, additional medical problems, and potentially death. That 1:3,000 number correlates to over 2,000 occurrences annually in the US alone. Mortality rates with retained guidewires is as high as 1 in 5.

There are detailed procedures in place to assure that guidewires are never inadvertently left in patients. These include checklists, instrument counts, and careful training. Nonetheless, these events continue to happen due to human error. The most common cause is catheter advancement into the body over the wire before the guidewire is threaded the entire length of the catheter so that the lagging or doctor end of the wire can be gripped by the user and held in place during advancement. Consistent factors noted in many investigations include operator fatigue, distractions, emergency situations, and inexperience. These human factors cause safety steps to be forgotten or skipped in the interest of expediency or deviated from due a confluence of uncommon events. Almost all safety steps in place require the operator to perform various safety checklists even though human factors often reduce their reliability. Very little safety engineering has been done to modify equipment and reduce the potential for human error.

The market for guidewires is now global and growing. Market data shows this market to be about $1 billion globally each year and growing at a CAGR of 8.2%.

An exemplary set of steps for installing a known catheter is provided below. (The same or similar procedures are used for many other types of operations in which a guidewire is used to place a catheter.)

1. A needle is inserted into the blood vessel at a location on the body where the catheter is to be placed.
2. Guidewire is pushed through the needle into the blood vessel.
3. Guidewire continues to be pushed into the blood vessel to the appropriate depth so that the guidewire remains in the vessel once the needle is removed.
4. The needle is removed over the exposed or doctor end of the guidewire while leaving the guidewire in place.
5. A catheter is advanced over the exposed or doctor end of the guidewire and into position so that the leading tip of the catheter is completely in the blood vessel.
6. The guidewire is removed through the catheter and discarded, leaving the catheter in proper position.
7. The catheter is secured in place with sutures and/or adhesive dressing to maintain proper position.

FIGS. 3A and 3B illustrate (using different shading techniques for clarity) a guidewire similar to a known guidewire where a portion of the guidewire has been shown segmented for illustration purposes only. In the left-hand portion of FIG. 3A, the portion of the catheter to be inserted into the patient (i.e., the patient side portion of the guidewire) has a "J" shape to it. This is common in some guidewires—though not mandatory. The J shape helps offers a blunt leading edge so that the wire does not puncture the lining of the blood vessel and/or unintentionally perforates the vessel. The J shape is configured to be very flexible (i.e., have a low coefficient of springiness so that it can be easily straightened or bent during introduction and then return to its previous shape).

FIG. 3C is an expanded view of the segmented portion of the guidewire of FIGS. 3A and 3B and illustrates the internal and external structure of a portion of the guidewire of FIGS. 3A and 3B. As shown in FIG. 3C, coils of the guidewire surround a straight inner wire core.

BRIEF DESCRIPTION OF THE DRAWINGS

The following description, given with respect to the attached drawings, may be better understood with reference to the non-limiting examples of the drawings, wherein.

DISCUSSION OF THE PREFERRED EMBODIMENTS

Figure 1:
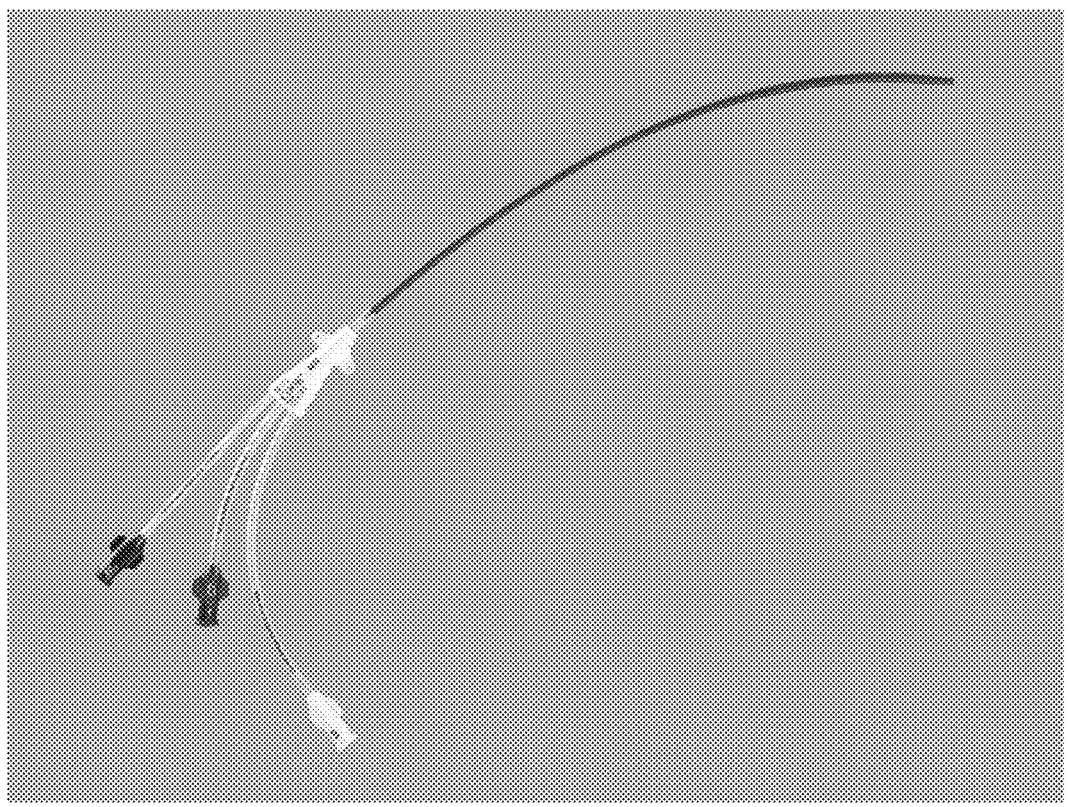
FIG. 1 is an illustration of an exemplary, known 3 lumen catheter prior to insertion into a patient.
Figure 2A:
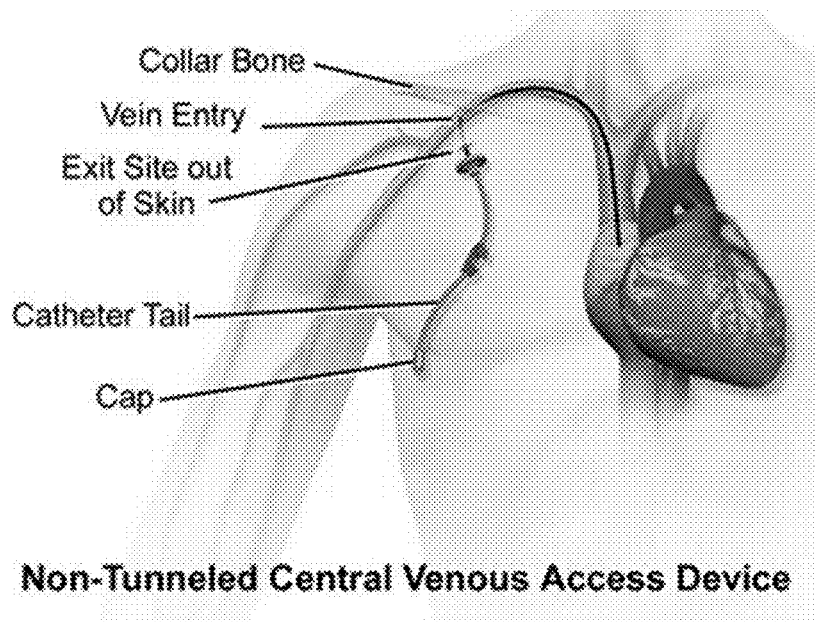
FIG. 2A is an illustration of a catheter as used when inserted into a patient.
Figure 2B:
FIG. 2B is a picture of a patient into whom a catheter has been inserted.
Figure 3A:
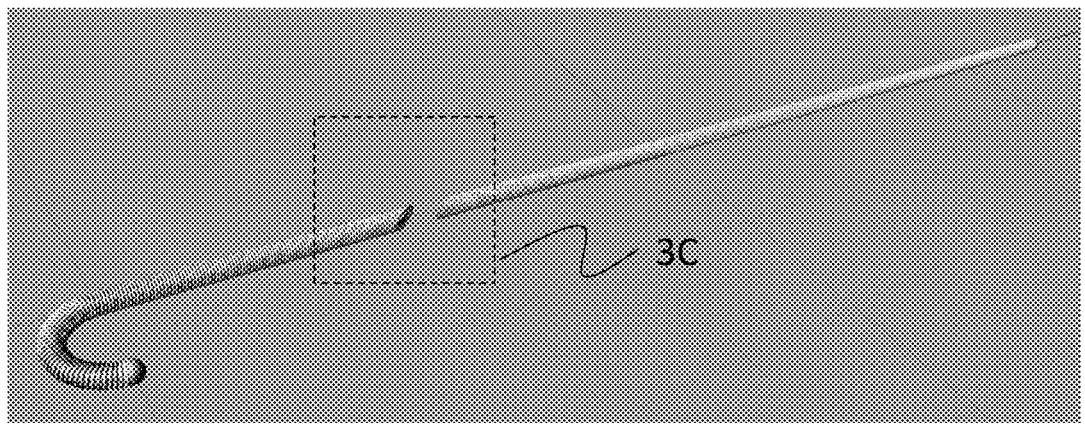
FIGS. 3A and 3B are illustrations of a known guidewire (where two different shading models were used to accentuate various aspects of the guidewire's construction) where a portion of the guidewire has been shown segmented for illustration purposes only.
Figure 3B:
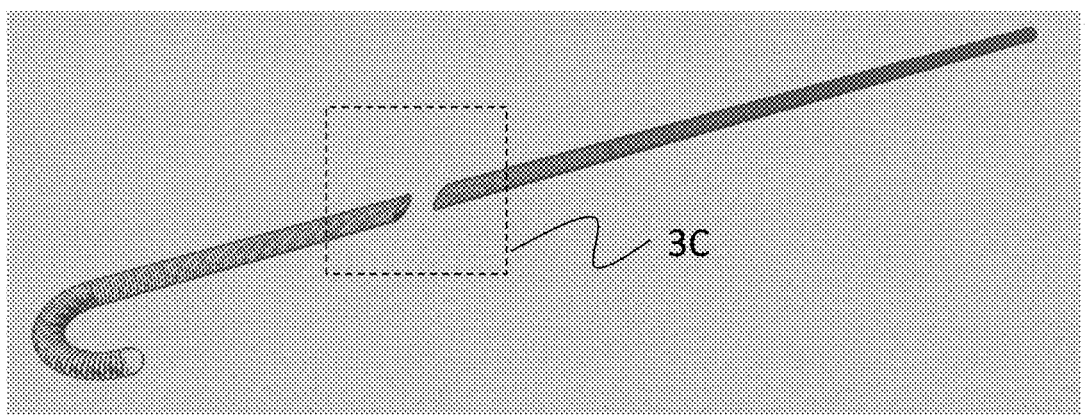
Figure 3C:
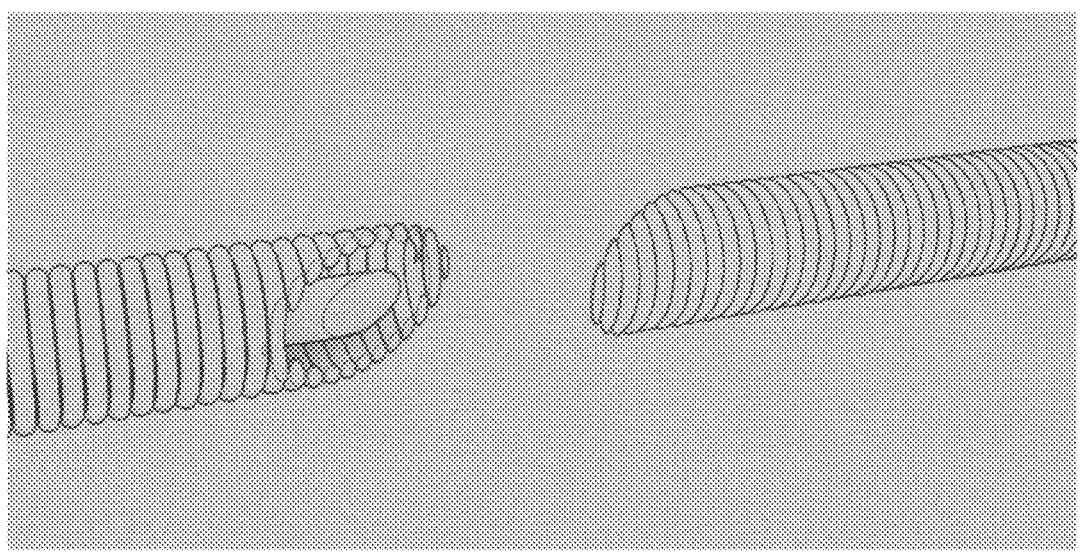
FIG. 3C is an expanded view of the segmented portion of the guidewire of FIGS. 3A and 3B and illustrates the internal and external structure of a portion of the guidewire.

The present invention is directed to a guidewire configured to reduce the incidence of medical accidents when using guidewires including, but not limited to, the incidence of guidewires accidentally being pushed completely into a patient by a catheter, guidewires accidently being left inside patients after the placement of central venous (and other) catheters, and guidewires accidently being left inside patients after removal of the catheter (at the end of an operation of other medical procedure). In particular, an intermediary portion (e.g., in the form of a new shape (referred to herein as "an obstruction portion") or an alternate (e.g., more flexible) material, or a series or parallel combination of at least one of both an obstruction portion and an alternate material) of the guidewire inhibits further advancement of the guidewire into the needle with pushing motion. (The intermediary portion can be implemented as an additional portion connected between the patient-side portion and the doctor-side portion of the guidewire as well.) When the intermediary portion is implemented as an obstruction portion, the obstruction portion has a reducible "diameter" (either temporarily or permanently) such that in its normal state the intermediary portion cannot pass into a needle, but, in the presence of a pulling force (and therefore in its "reduced diameter" state) the needle can be pulled backwards overtop the obstruction portion and the catheter can advance forward overtop the obstruction portion in accordance with the catheter placement described herein. As used herein, "diameter" is intended to mean the widest portion of a particular segment, in one or more planes, even if the shape is not circular.

A number of different configurations and/or embodiments are presented below. In one such embodiment, an obstruction portion has a diameter in its normal state of two (2) to three (3) times that of the patient end wire diameter with a length of 1 to 4 times the patient end wire diameter. Alternatively, longer lengths also can be used. However, numerous other intermediary portions (including obstruction portions) can be implemented based on the teachings of this disclosure. In a first configuration, the portions on either side of the obstruction portion are manufactured together to form an integrated guidewire (with an obstruction portion). In a second configuration, the portions on either side of the obstruction portion are manufactured separately and a joined, either permanently or temporarily before and/or during the process of inserting a catheter into a patient. Such a configuration will be referred to as a detachable configuration. The obstruction portion may be the same color as the rest of the guidewire or may be colored differently to aid the doctor in seeing it. Moreover, the colors of the two sides of the guidewire (the patient-side and the doctor-side) may be different for easier identification. Colored markings (or other visually identifiable changes in the guidewire) also may be used to indicate how much a guidewire has been advanced. For example, every 10 cm a number of markings is shown indicating the length inserted so far (e.g., a single blue stripe around the guidewire for 10 cm, two yellow stripes for 20 cm, three orange stripes for 30 cm and four red stripes for 40 cm).

A series of integrated guidewires will now be discussed although the teaching of the construction of the integrated guidewires can be applied to the construction of the detachable guidewires as well. In an integrated guidewire, the length of the wire "behind" the obstruction portion (i.e., the portion of the guidewire between the doctor and the obstruction portion (also referred to herein as the "doctor-side of the guidewire")) is sufficient such that it is greater than the length of the catheter and will extend out the "back" of the catheter (i.e., out the end of the catheter closer to the doctor and not inserted into the patient) before the tip of the catheter reaches the obstruction portion. The catheter can then be advanced over the obstruction portion by the doctor holding the end of the doctor-side of the guidewire. This is accomplished by a forward advancement of the catheter alone or in combination with a manipulation of the wire through pulling, twisting, pushing, or combination thereof. This action on the exposed end of the doctor-side of the guidewire causes the large obstruction portion shape to collapse (or temporarily reduce its diameter) allowing the catheter to slide over the obstruction portion of the guidewire. Once the catheter is fully in place in the body, the guidewire is pulled fully out of the catheter and body to be discarded.

An exemplary set of steps for installing a catheter using an integrated catheter is provided below, although those of skill in the art will know that additional and/or alternative steps may be used. (The same or similar procedures are used for many other types of operations in which a guidewire is used to place a catheter.)

1. A needle is inserted into the blood vessel at a location on body where the catheter is to be placed.
2. The end of the patient side of the guidewire is pushed through the needle into the blood vessel.
3. The patient side of the guidewire continues to be pushed into the blood vessel to the appropriate depth so that the guidewire remains in the vessel once the needle is removed.
4. The needle is removed over the guidewire (while leaving the guidewire in place) by temporarily reducing the diameter of the obstruction portion (e.g., by pulling, pushing or twisting a portion of the guidewire) while the needle passes over the obstruction portion. The obstruction portion can then return to its normal state (with its "normal diameter") once the needle has passed over the obstruction portion.
5. A catheter is advanced along the guidewire (starting at the doctor-side) and into position so that the leading tip of the catheter is completely in the blood vessel. To do so, the diameter of the obstruction portion is again reduced (e.g., by pulling, pushing or twisting a portion of the guidewire) while the catheter passes over the obstruction portion. The obstruction portion can then return to its normal state (with its "normal diameter") once the catheter has fully passed over the obstruction portion.
6. In general, the guidewire is removed through the catheter, and the guidewire as a whole is discarded, leaving the catheter in proper position.
7. The catheter is secured in place with sutures and/or adhesive dressing to maintain proper position.

Figure 4A:
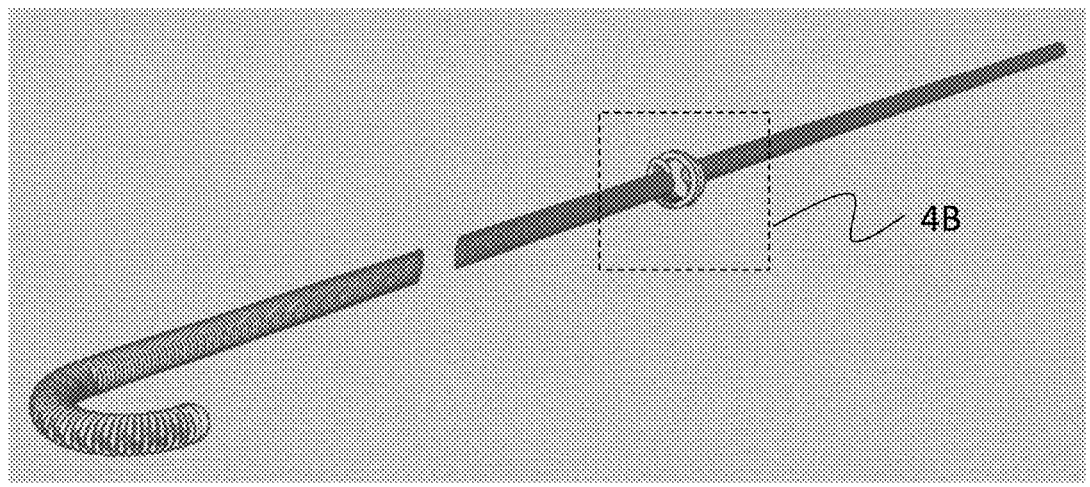
FIG. 4A is an illustration of a first exemplary guidewire according to the present invention where a portion of the guidewire has been shown segmented for illustration purposes only.

FIG. 4A illustrates a first exemplary guidewire according to the present invention where a portion of the guidewire has been shown segmented for illustration purposes only. In the left-hand portion of FIG. 4A, the portion of the catheter to be inserted into the patient has a "J" shape to it. This is common in some guidewires—though not mandatory. The J shape helps offers a blunt leading edge so that the wire does not puncture the lining of the blood vessel and/or unintentionally perforates the vessel. The J shape is configured to be very flexible (i.e., have a low coefficient of springiness so that it can be easily straightened or bent during introduction and then return to its previous shape).

Figure 4B:
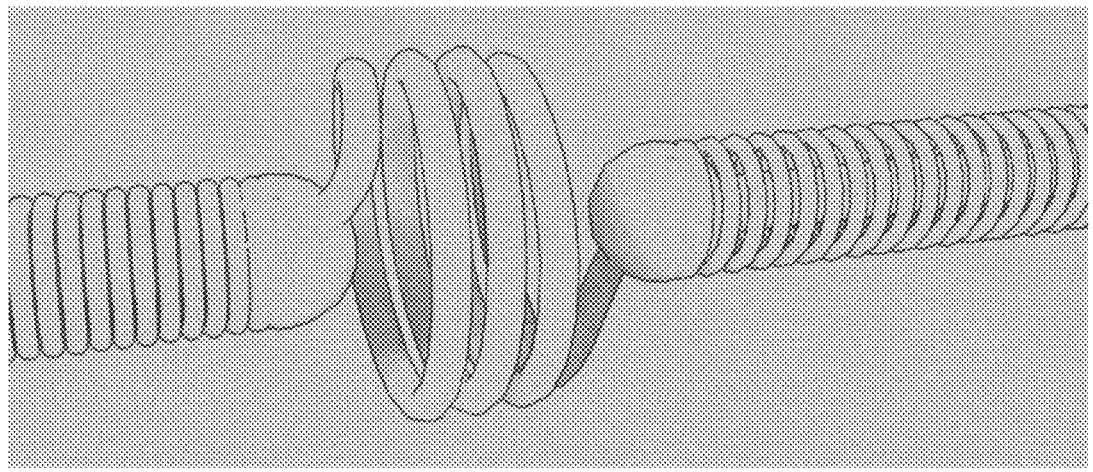
FIG. 4B is an expanded view (as compared to FIG. 4A) of an obstruction portion of a guidewire (having a reducible diameter) where the diameter of the obstruction portion is in its normal state (i.e., when the diameter is not reduced)

FIG. 4B is an expanded view of an obstruction portion of the guidewire of FIG. 4A and which also illustrates the portions of the guidewire on either side of the obstruction portion. As can be seen from FIG. 4B, the number of twists per inch and the spacing between twists on the two sides of the obstruction portion need not be the same, but they can be. In one embodiment, each wrap of the coils (before and after the obstruction portion) touch each other. However, the number of twists should allow the guidewire to be flexible (acting much like a spring.) The coils of the obstruction portion are larger than the width of the needle so that the needle will not pass over the obstruction portion if the coils are not temporarily deformed to allow the needle's progress to continue. Thus any normal pushing motion on the guidewire into the patient will be prevented when the obstruction portion gets to the needle—preventing a retained guidewire situation. When the needle is ready to be removed, by simply pulling the need out of the vein of the patient and then grasping the patient side of the guidewire, one can pull the needle over the obstruction portion and off the guidewire. The obstruction portion will be reduced in diameter when the needle is pulled over it. But the guidewire cannot be pushed into the needle past the obstruction portion.

The coils of the guidewire preferably surround a straight inner wire core that provides additional rigidity to the guidewire. The inner wire and the outer coils need not be made of the same materials, but they may be. Alternatively, the guidewire can be constructed with the outer coils only and without the inner core, or could be constructed of a single core material without any additional surrounding coils.

Figure 4C:
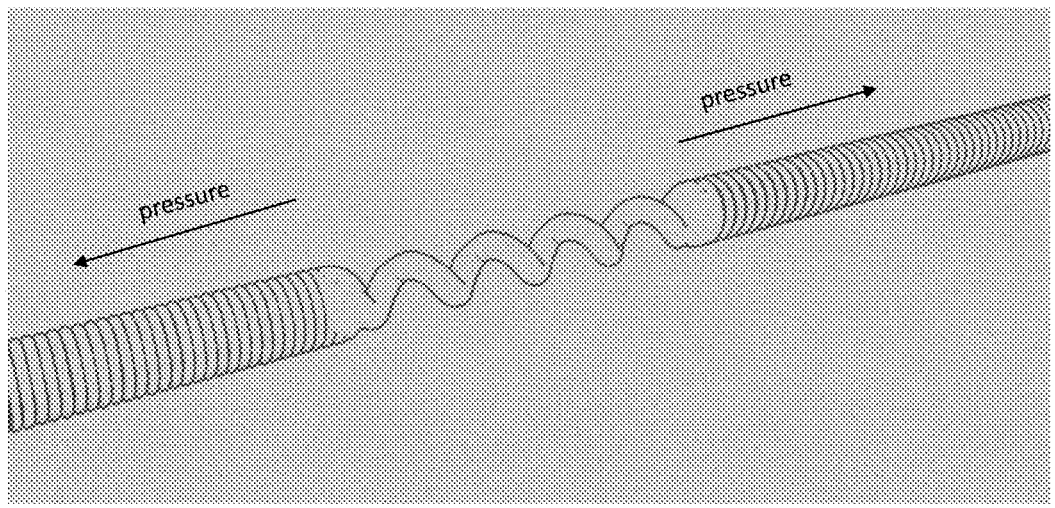
FIGS. 4C and 4D are second and third expanded views of the obstruction portion of FIG. 4A (where two different shading models were used to accentuate various aspects of the obstruction portion's construction) when the diameter of the obstruction portion has been temporarily reduced by applying a pulling force in opposite directions towards the two ends of the guidewire.
Figure 4D:
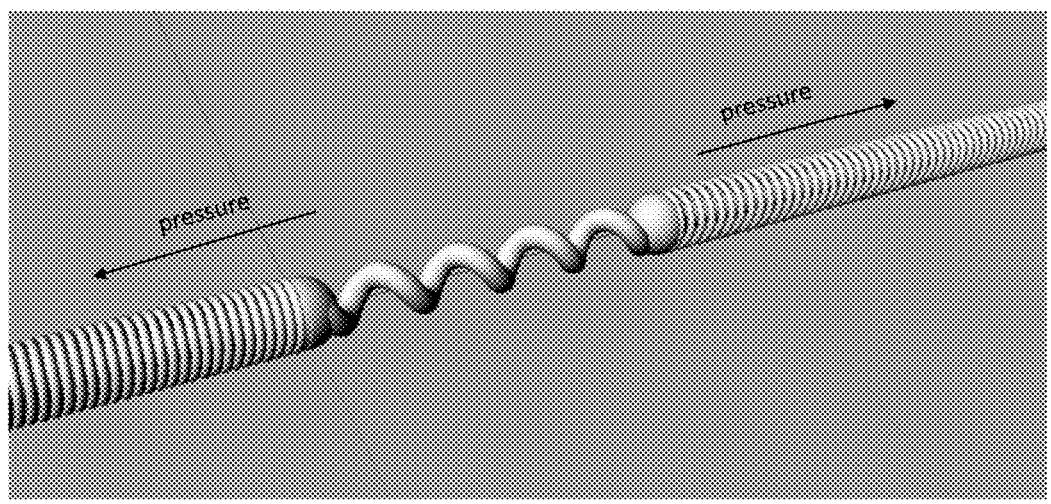

FIGS. 4C and 4D are second and third expanded views of the obstruction portion of FIG. 4A when the diameter of the obstruction portion has been temporarily reduced by applying a pulling force in opposite directions towards the two ends of the guidewire. The diameter of the obstruction portion returns to larger than the inner diameter of the needle and/or catheter after the pulling force is removed. As described herein, the diameter of other obstruction portions can be reduced by actions other than pulling, such as pushing or twisting a portion of the guidewire. The obstruction portion need not return to exactly the same size as before its diameter was reduced. Rather, the diameter may change slightly as a result of the pushing, pulling and/or twisting.

Figure 5A:
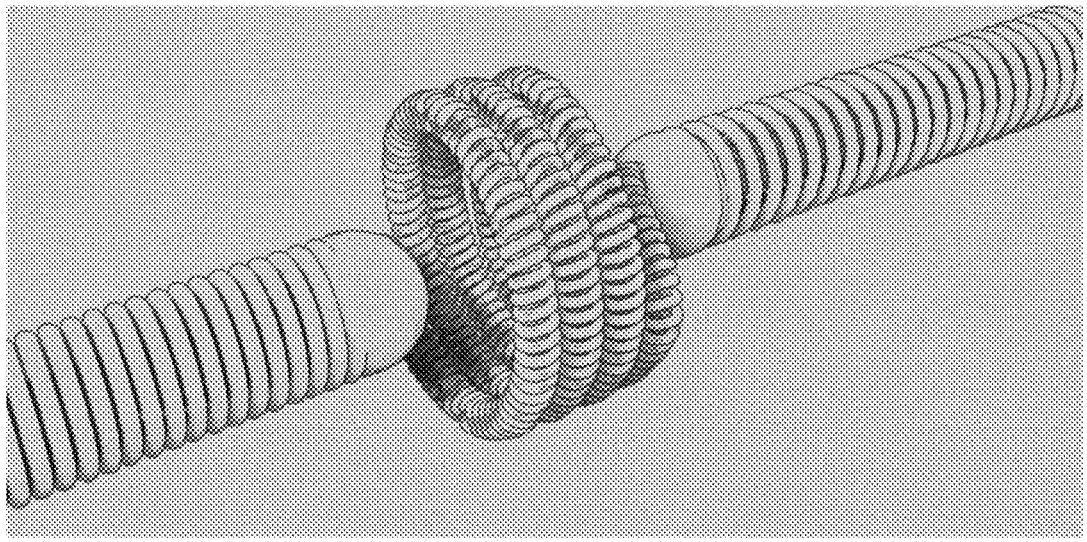
FIGS. 5A and 5B are first and second expanded views of an obstruction portion of a second exemplary guidewire (where two different shading models were used to accentuate various aspects of the obstruction portion's construction)
Figure 5B:
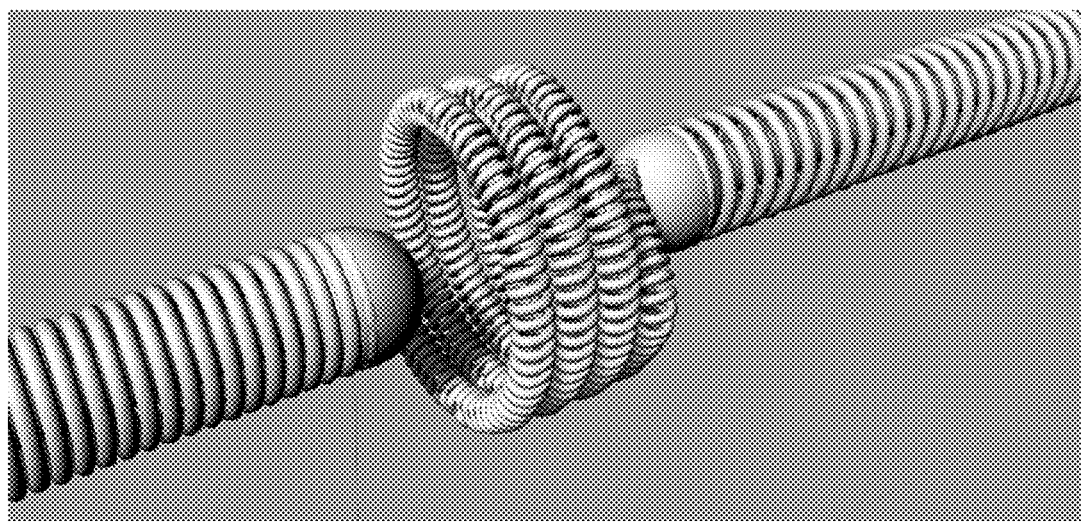

FIGS. 5A and 5B are first and second expanded views of an obstruction portion of a second exemplary guidewire (where two different shading models were used to accentuate various aspects of the obstruction portion's construction). This "spring around a spring" configuration allows for very soft and flexible obstruction portion. Pulling on the right end (relative to the left end) and the obstruction portion stretches out dramatically decreasing the diameter to about that of the other sides of the guidewire. In one embodiment, the spring spacing on the guidewires are configured so that each wrap of the spring touches the adjacent spring wire wrap. Alternatively, a slight spacing between can be used (and in this application is used) so that one can easily see the construction of the guidewire as a helical spring and with an inside wire. The guidewire that enters the body is on the left. The right side is the side that will stay outside the body. On the right side—the spring windings are even spaced a little further signifying that the spacing for this far end piece does not have to be the same as the guidewire that enters the body. Furthermore, the left and right sides can have different flexibility characteristics as only the left side enters the body.

Figure 6A:
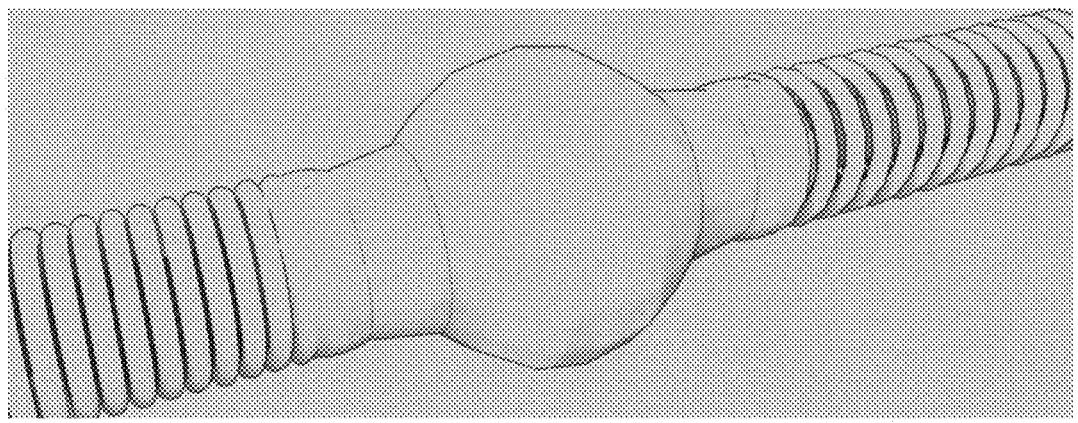
FIG. 6A is a first expanded view of an obstruction portion of a third exemplary guidewire.
Figure 6B:
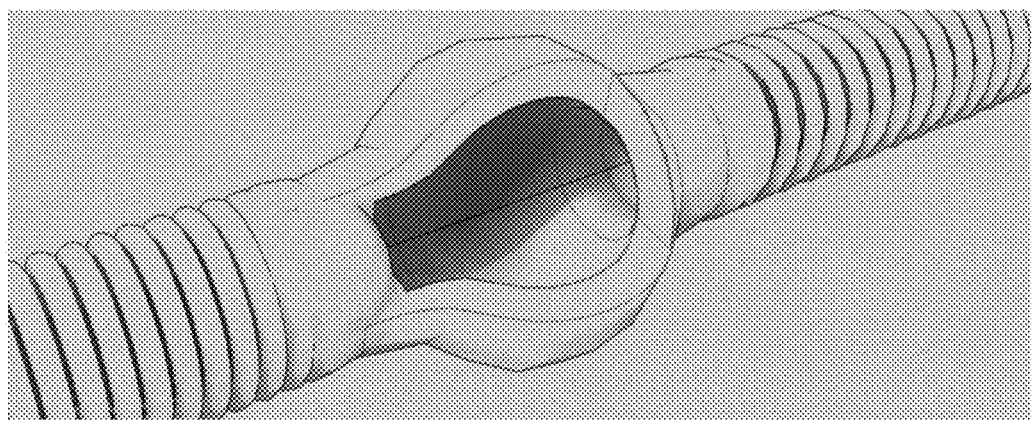
FIGS. 6B and 6C are first and second cut-away views of the obstruction portions of the third exemplary guidewire of FIG. 6A (where two different shading models were used to accentuate various aspects of the obstruction portion's construction)
Figure 6C:
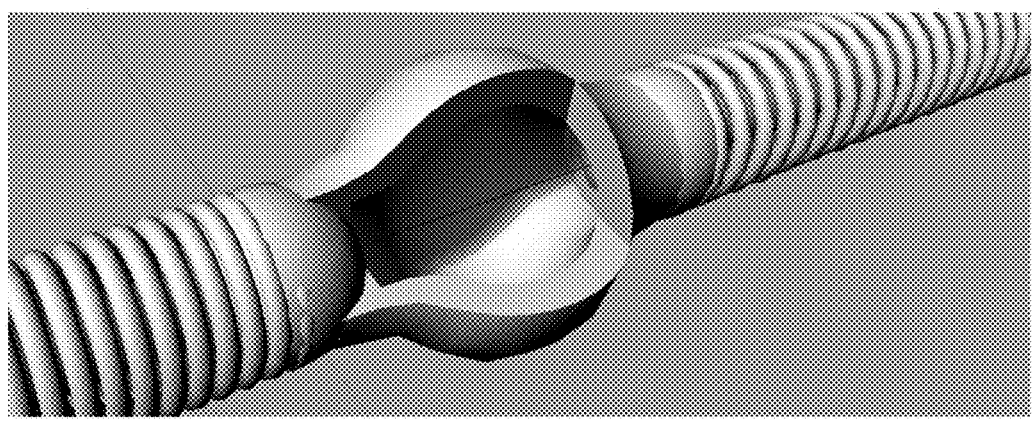

FIG. 6A is a first expanded view of an obstruction portion of a third exemplary guidewire. In this embodiment, the obstruction portion includes a spherical shape that shrinks in diameter when the guidewire is pulled on. The sphere can be hollow or a deformable solid. Exemplary materials for the spherical shape include foam, rubber or any elastomer. Additional deformable shapes are also possible, such as abutted pyramids or oblong cylinders, either of which are either hollow or deformable solids. FIGS. 6B and 6C are first and second cut-away views of the obstruction portions of the third exemplary guidewire of FIG. 6A in an embodiment where the spherical shape is hollow. In such a configuration, the hollowness or wall thickness of the sphere can be configured to result in a desired amount of force having to be exerted on the sphere to allow the needle and/or catheter to deform it when pass over.

Figure 7A:
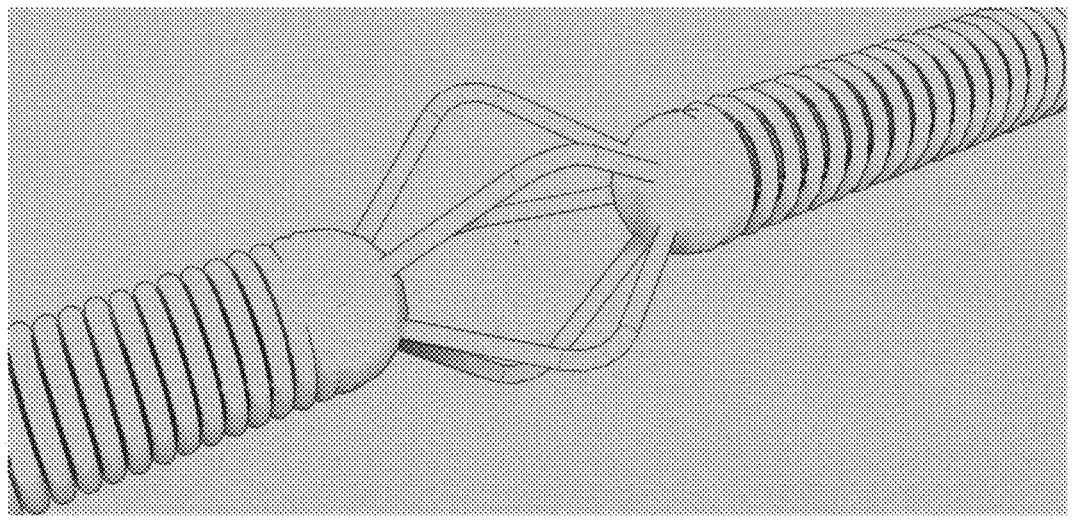
FIGS. 7A and 7B are first and second expanded views of an obstruction portion of a fourth exemplary guidewire (where two different shading models were used to accentuate various aspects of the obstruction portion's construction)
Figure 7B:
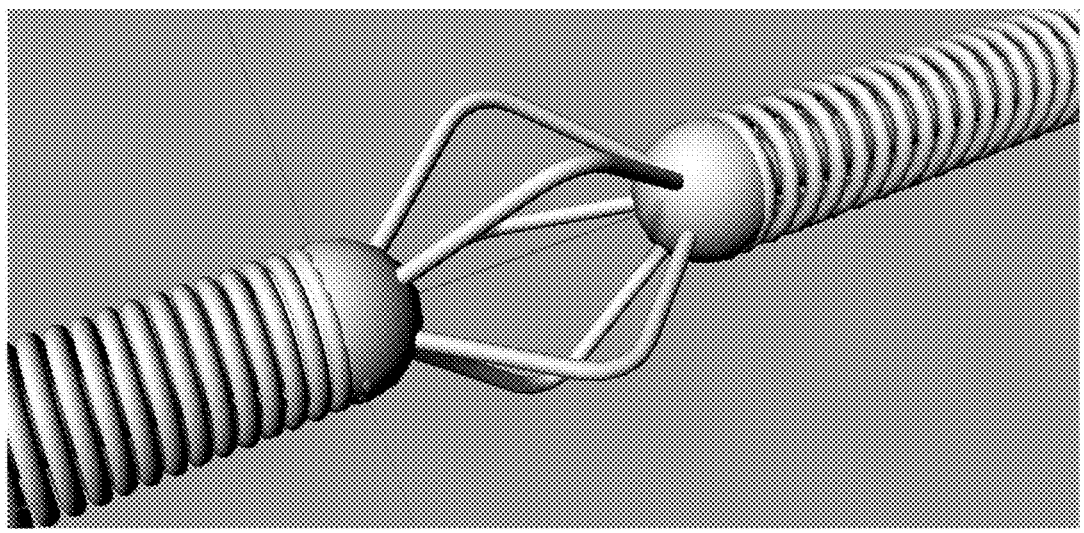

FIGS. 7A and 7B are first and second expanded views of an obstruction portion of a fourth exemplary guidewire. In this embodiment, the obstruction portion uses a series of a light springs—shown in the exemplary (non-limiting) embodiment with 5 radially spaced around (although other numbers of springs could be used). Pulling on the right side of the guidewire results in the diameter of the obstruction portion shrinking and allowing the needle to slide off and the catheter to slide over to then proceed into the body.

Figure 8A:
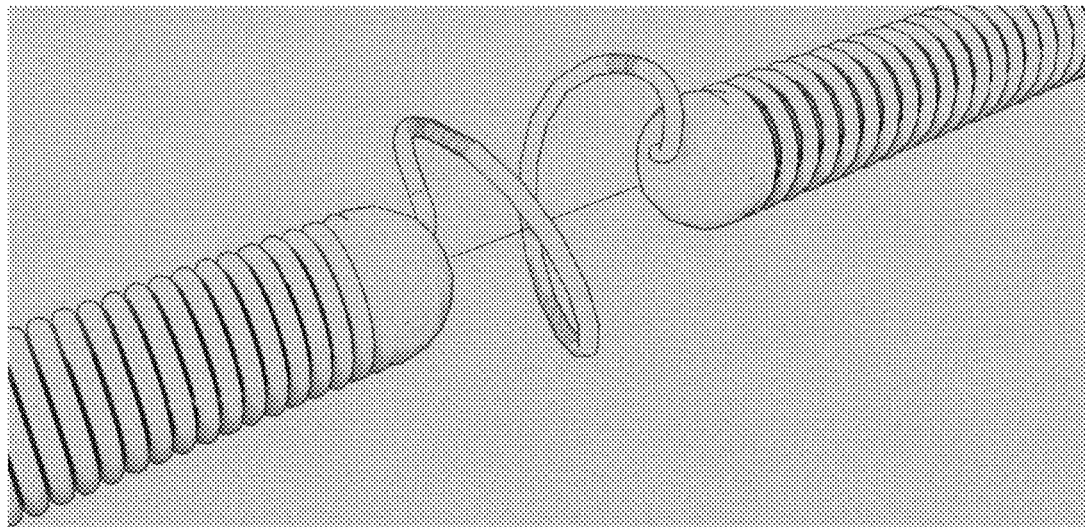
FIGS. 8A and 8B are first and second expanded views of an obstruction portion of a fifth exemplary guidewire (where two different shading models were used to accentuate various aspects of the obstruction portion's construction)
Figure 8B:
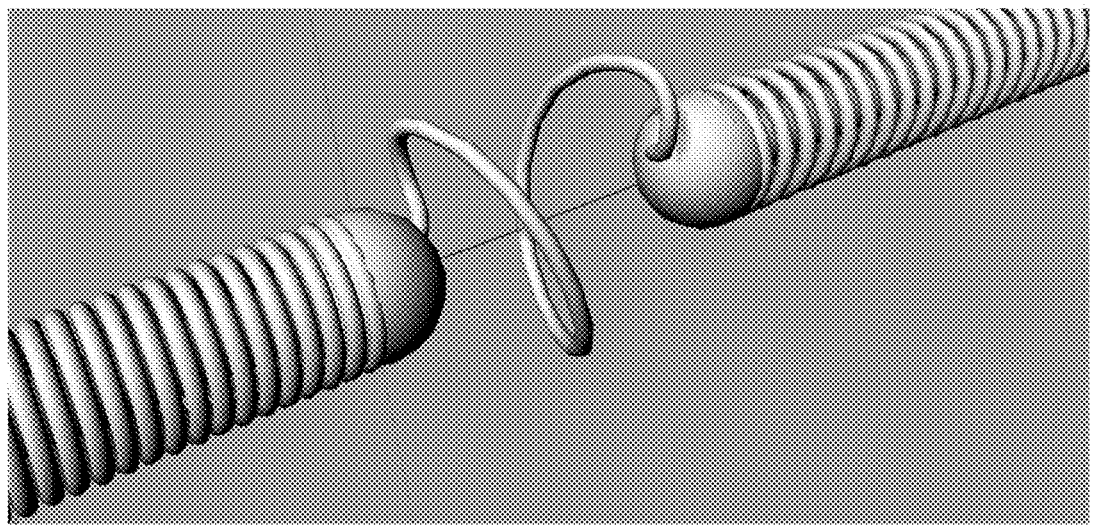

FIGS. 8A and 8B are first and second expanded views of an obstruction portion of a fifth exemplary guidewire where a spring with a full 360° single turn connects both sides. Other rotational amounts other than 360° (as shown in the non-limiting example) can be used. Pulling on the right side of the guidewire results in the diameter of the obstruction portion shrinking and allowing the needle to slide off and the catheter to slide over to then proceed into the body.

Figure 9A:
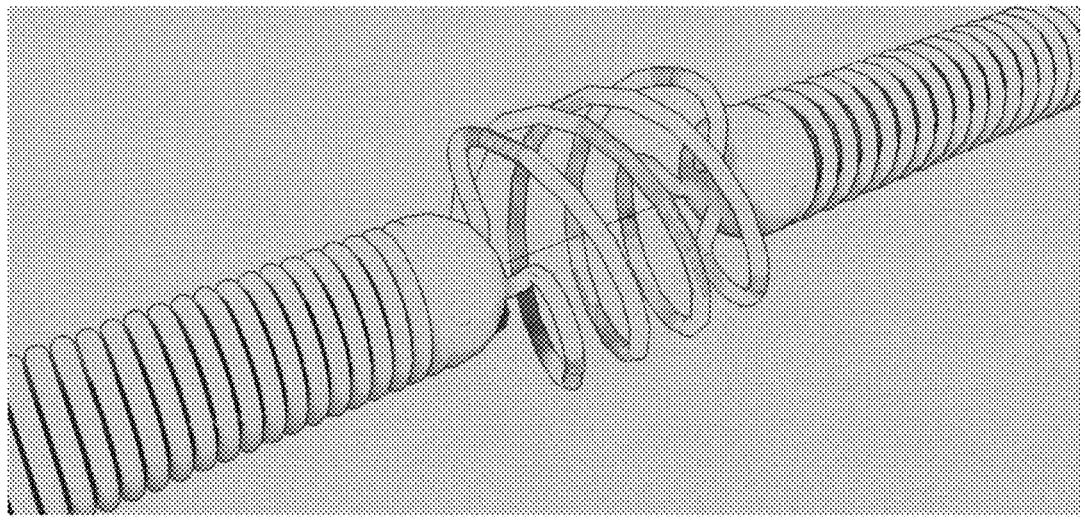
FIGS. 9A and 9B are first and second expanded views of an obstruction portion of a sixth exemplary guidewire (where two different shading models were used to accentuate various aspects of the obstruction portion's construction)
Figure 9B:
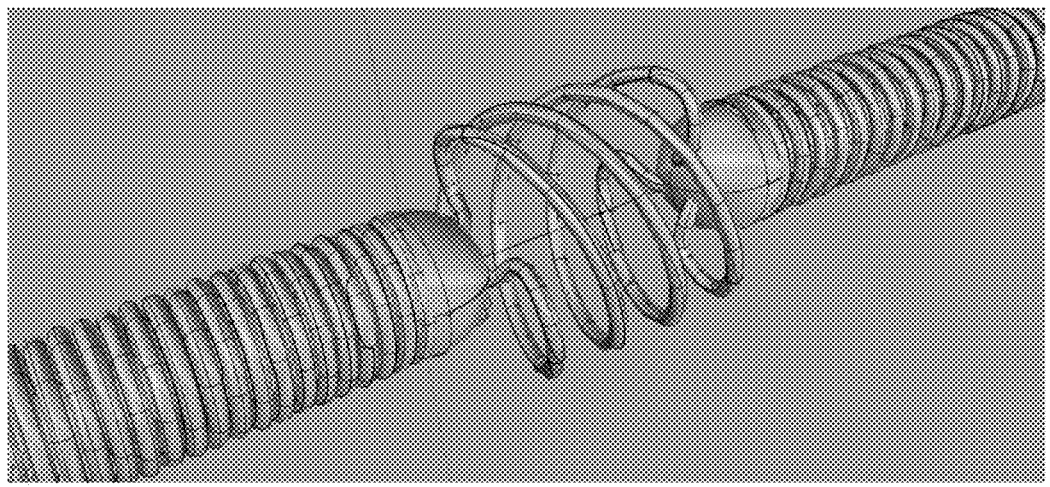

FIGS. 9A and 9B are first and second expanded views of an obstruction portion of a sixth exemplary guidewire where the obstruction portion is constructed as 3 single turns springs arranged 120° apart. Similarly, other rotational spacings (other than 120°) and other numbers of turns can be used. By arranging them in an intertwined configuration, a bit more rigidity and stability can be provided if needed. Pulling on the right side of the guidewire results in the diameter of the obstruction portion shrinking and allowing the needle to slide off and the catheter to slide over to then proceed into the body.

Figure 10A:
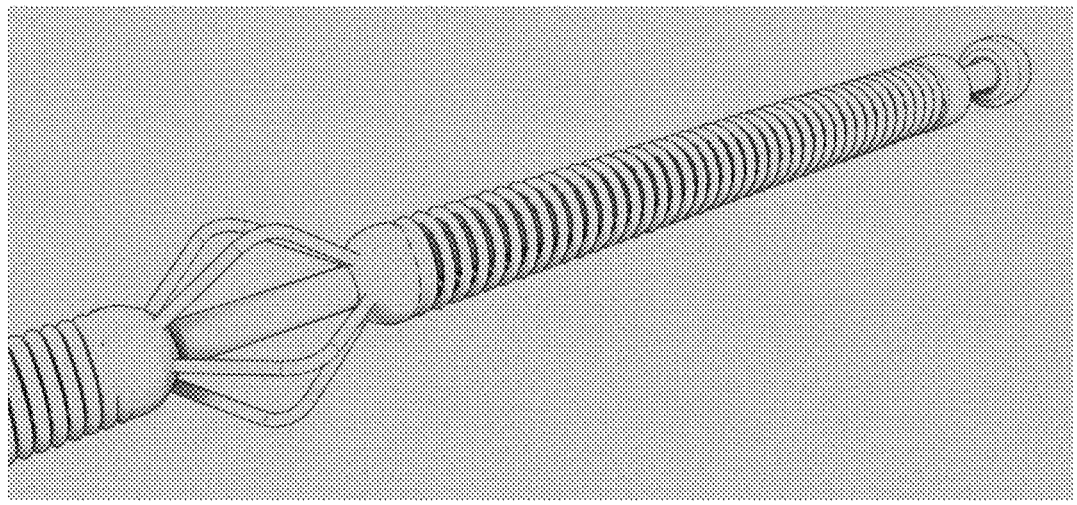
FIGS. 10A and 10B are first and second expanded views of an obstruction portion and plunger of a seventh exemplary guidewire (where two different shading models were used to accentuate various aspects of the obstruction portion's construction) in which the plunger is included at the doctor-side of the guidewire to temporarily flatten out the obstruction portion when needed.
Figure 10B:
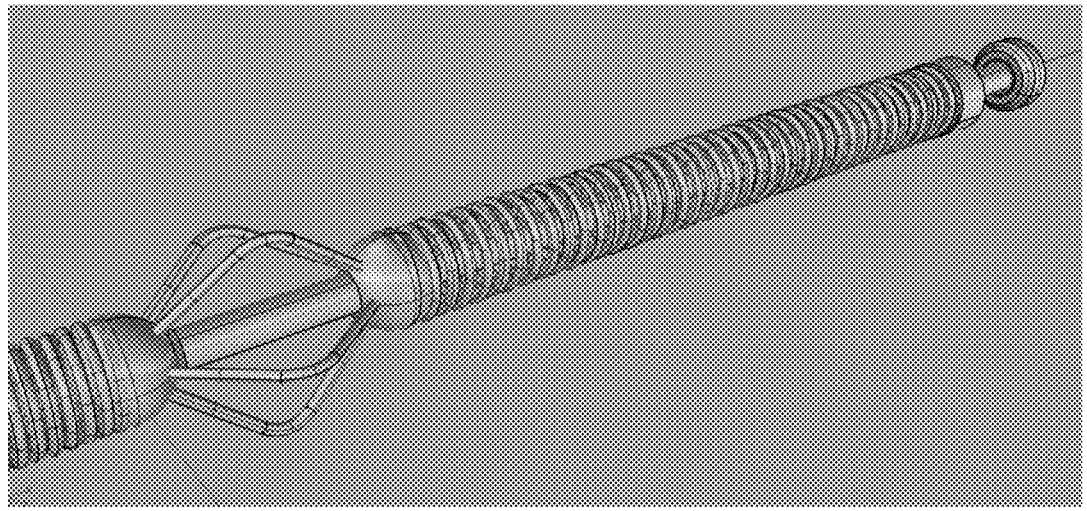

FIGS. 10A and 10B are first and second expanded views of an obstruction portion and plunger of a seventh exemplary guidewire. The plunger is included at the right side (i.e., the doctor-side) of the guidewire to temporarily flatten out the obstruction portion when needed. Furthermore, any of the previously shapes can be made with a plunger (on the right) that pushes the other ball away causing a pulling action on the obstruction portion. Such a plunger can be used with almost any of the other shapes that require a pulling action to shrink the diameter. The advantage of this approach is that all the pulling/pushing is done at the far-right side. Other configurations described herein required one to pull the right side relative to the left side being held in place.

Figure 11A:
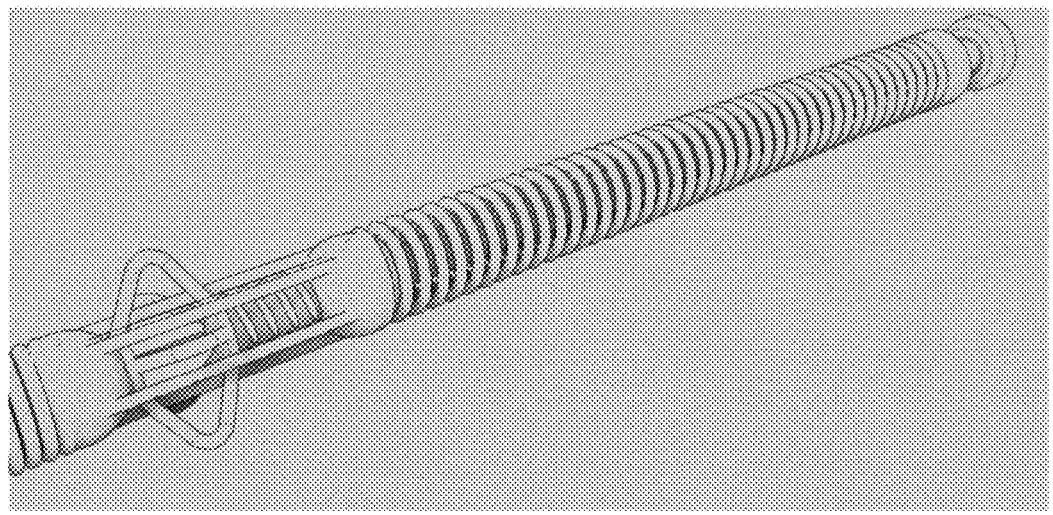
FIGS. 11A and 11B are first and second expanded views of an obstruction portion and pulling device of a eighth exemplary guidewire (where two different shading models were used to accentuate various aspects of the obstruction portion's construction) in which the pulling device is included at the doctor-side of the guidewire to temporarily flatten out and reduce the diameter of the obstruction portion when needed.
Figure 11B:
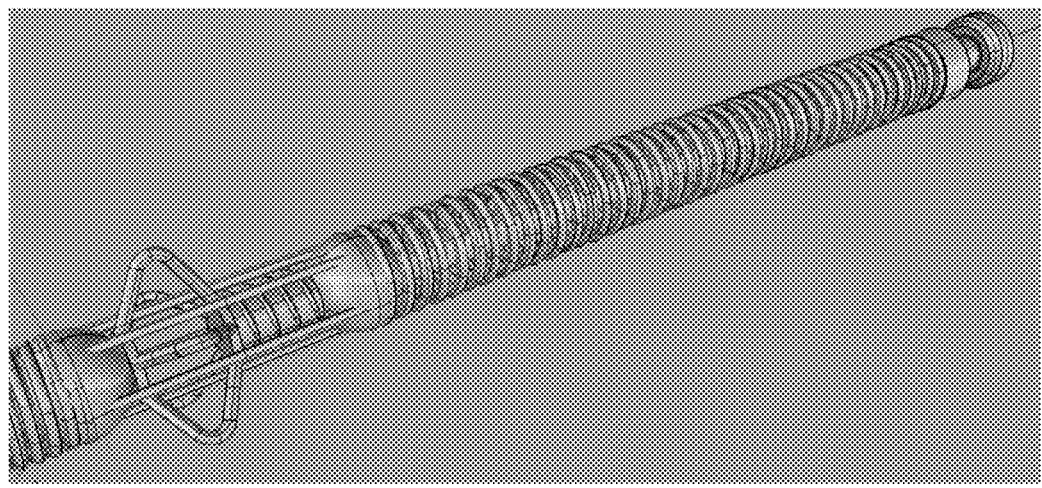
Figure 11C:
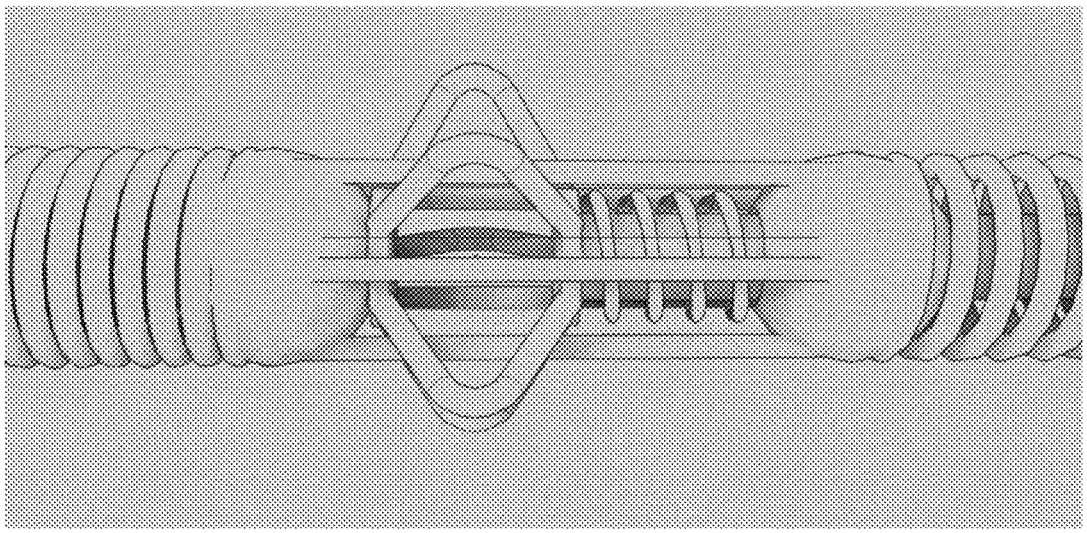
FIGS. 11C and 11D are first and second expanded side views of the obstruction portion of FIGS. 11A and 11B (where two different shading models were used to accentuate various aspects of the obstruction portion's construction) showing in greater detail the pulling device included at the doctor-side of the guidewire to temporarily flatten out and reduce the diameter of the obstruction portion when needed.
Figure 11D:
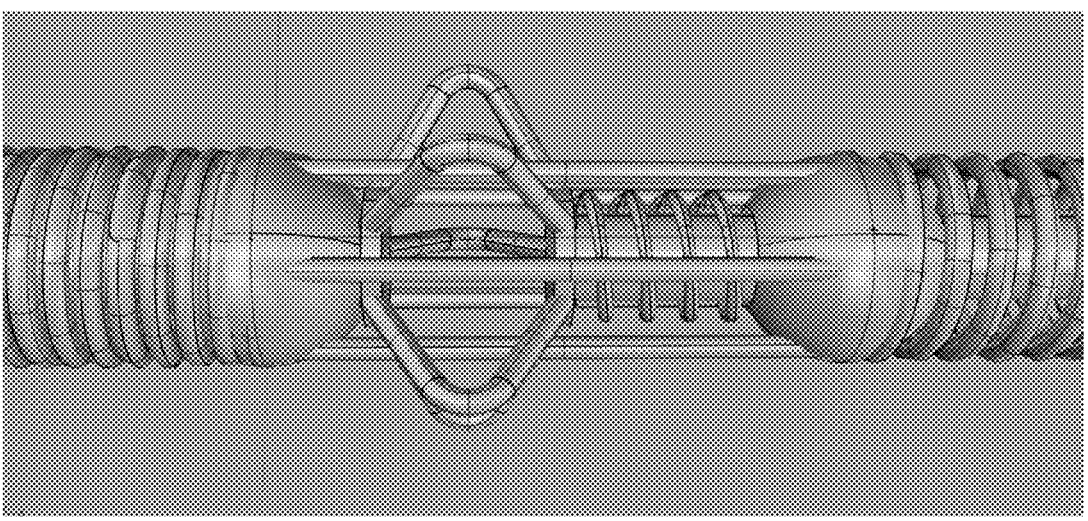

FIGS. 11A and 11B are first and second expanded views of an obstruction portion and pulling device of a eighth exemplary guidewire in which the pulling device is included at the doctor-side of the guidewire to temporarily flatten out the obstruction portion when needed. In this (and other pulling configurations) the obstruction portion is flattened (e.g., the springs are stretched lowering the diameter) by pulling at the doctor end. As shown in greater detail in FIGS. 11C and 11D, cross piece rods (e.g., 5 rods) connecting the two spheres keep the spheres at a constant spacing. Just the center bent spring section lowers reducing the diameter of the obstruction portion. To aid in providing the pulling action in a one-handed fashion, the pulling action can be performed by using a level (not shown) pushed by the doctor's thumb or by providing a gap in the end (not shown) into which the doctor can place a thumb to facilitate the pulling action.

Figure 12A:
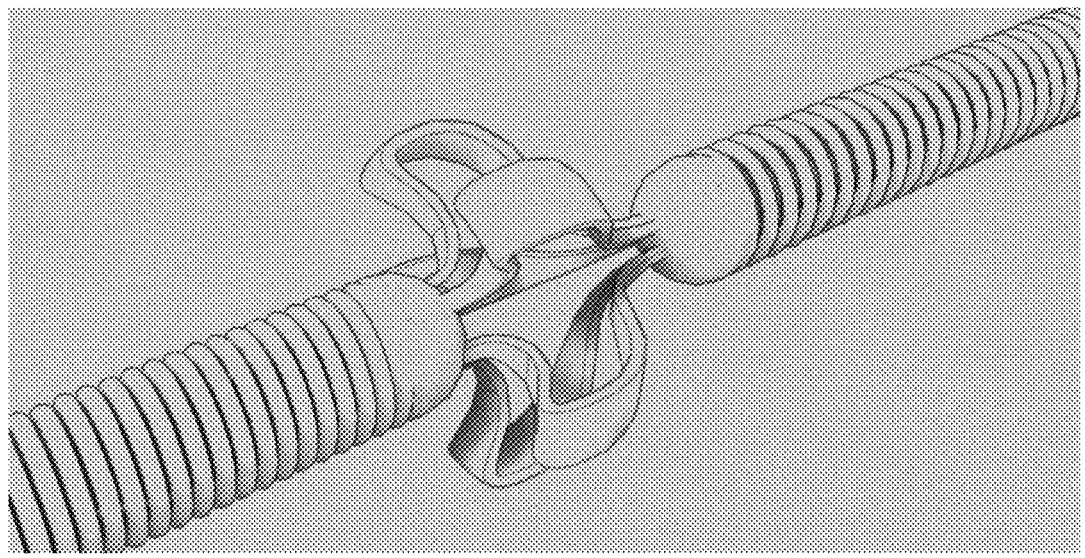
FIGS. 12A and 12B are first and second expanded views of an obstruction portion of a ninth exemplary guidewire (where two different shading models were used to accentuate various aspects of the obstruction portion's construction)
Figure 12B:
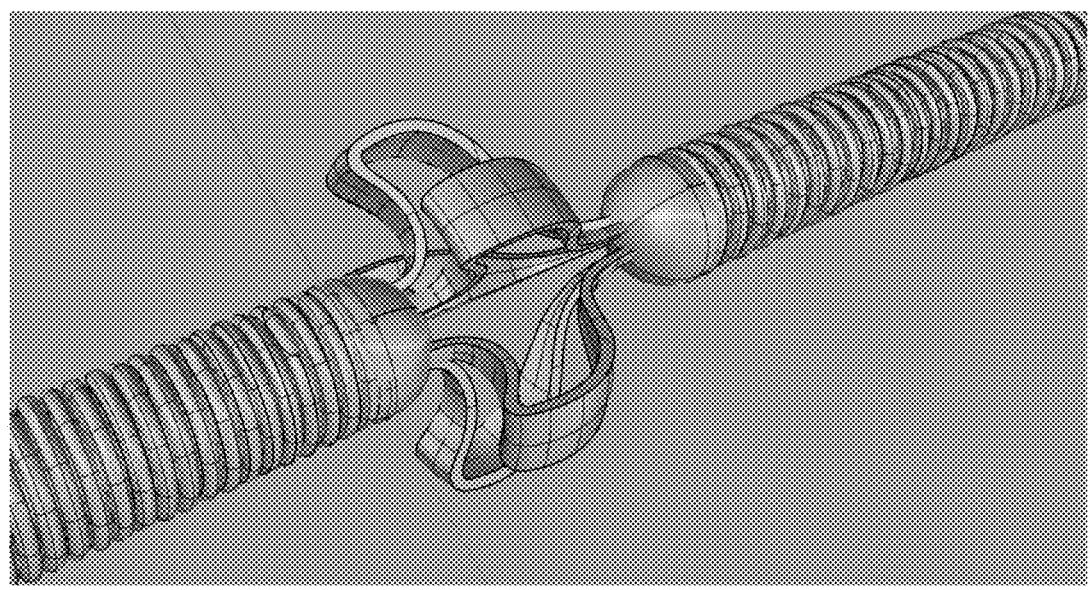

FIGS. 12A and 12B are first and second expanded views of an obstruction portion of an ninth exemplary guidewire. This obstruction portion preferably is made from an elastomeric compound which naturally rests in its illustrated expanded shape (or any other similar type shape). The shape is configured so that it is difficult to push through a small opening of a needle—but will be easily reduced in diameter when the right end is pulled. The dimensions of the embodiment of FIGS. 12A and 12B are such that when the system is pulled—the circumference of the middle section when each of the 5 sections is touching is just about the circumference of the wires—thus allowing the needle to slide off and the catheter to slide over it easily. The shape is shown non-symmetrical—but could be symmetrical as well.

Figure 13A:
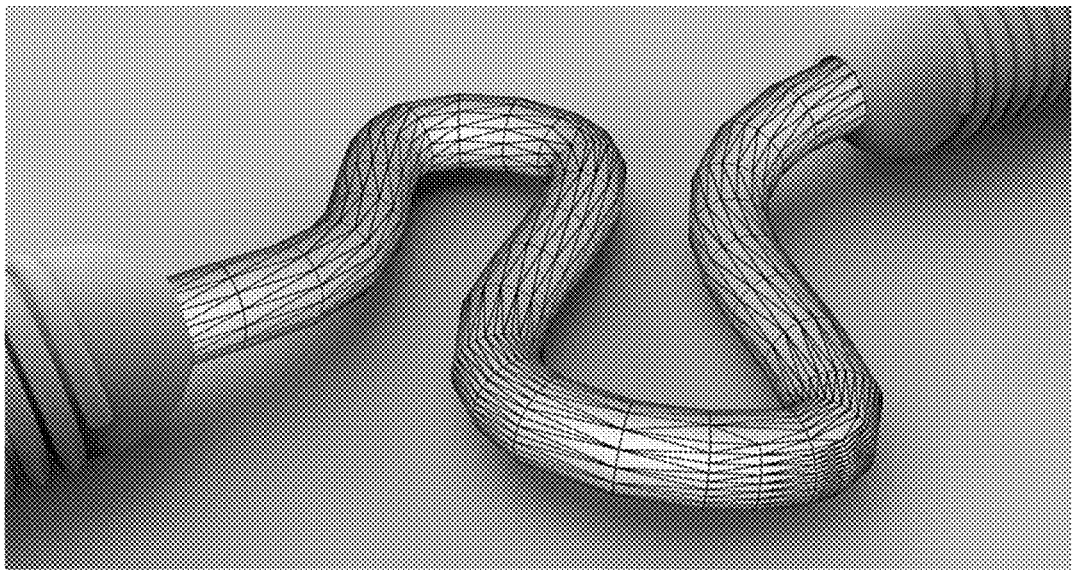
FIG. 13A is an expanded view of a first "flimsy string" acting as an intermediary portion of a tenth exemplary guidewire (where the lack of uniformity of the bends is intended to connote that the flimsy string does not hold a particular shape and lies flat when laid down)
Figure 13B:
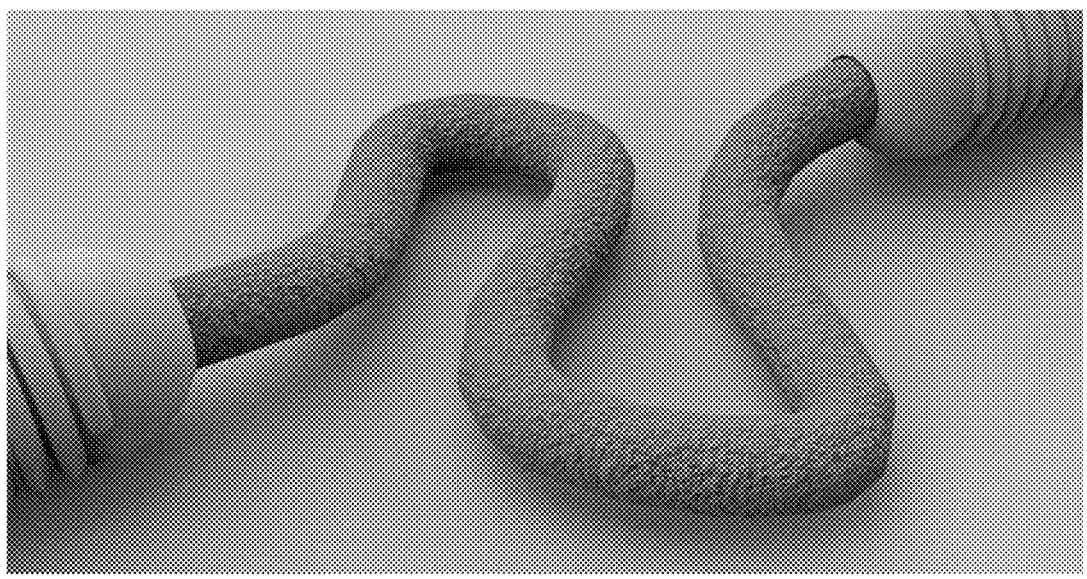
FIG. 13B is an expanded view of a second "flimsy string" acting as an intermediary portion of a tenth exemplary guidewire (where the lack of uniformity of the bends is intended to connote that the flimsy string does not hold a particular shape and lies flat when laid down, and where the texturing of the material is intended to accentuate that the flimsy string is made, in the illustrated embodiment, of a woven or braided material)

FIGS. 13A and 13B are first and second expanded views of a tenth exemplary guidewire having an intermediary portion. The intermediary portion includes at least one material interposed between and connected to both ends of the guidewire. Such a configuration makes it more difficult to push this material through the needle opening, but the needle can be pulled back off this intermediary portion and off the doctor-end. Likewise, the catheter could be put into place by pulling on the doctor end as the catheter is being pushed down the guidewire and over the intermediary portion. In the embodiment of FIGS. 13A and 13B, the intermediary portion is a "flimsy" or "wet noodle"-like material (e.g., a string-like or cord-like material) with essentially no rigidity (referred to as a "non-rigid portion") such that initially pushing on the doctor-side portion of the guidewire as the doctor-side portion becomes exposed in the dispenser does not drive the patient-side portion of the guidewire into the needle (or patient) (because the non-rigid portion is not rigid enough to drive the patient-side portion forward). (Although a doctor could advance the doctor-side portion twice the length of the non-rigid portion such that tension on the non-rigid portion would begin pulling the patient-side portion forward, the total cross section (or diameter) of the non-rigid portion side-by-side with the patient-side portion would be bigger than the opening diameter of the needle at that point and the non-rigid portion would not advance into the needle.) The non-uniformity of the bends is intended to connote that the flimsy string does not hold a particular shape on its own.

Various configurations are possible when constructing an intermediary portion, such as is shown in FIGS. 13A and 13B. A cord portion acting as an intermediary portion can be single- or multi-stranded and made from any of a number of fiber materials (e.g., polyimides (nylons), polyester, acrylic, polyolefin, carbon, graphite, fluoropolymer, Kevlar, and any natural material (e.g., cotton)). Moreover, the cord portion can include multiple parallel strands, including braided or twisted strands. It further can be constructed from a combination (or blend) of 2 or more fibers (braided, twisted, etc.) to further enhance needed characteristics. Likewise, it can have any number of cross-sections including, but not limited to, round or rectangular (as would be produced by a webbing). The cord portion further can be coated to enhance strength, abrasion resistance, stiffness, etc.

The intermediary portion may be separately manufactured from the patient-side and doctor-side of the guidewire and then attached between the patient-side and doctor-side of the guidewire using any number of physical or chemical bonding or attachment mechanisms. For example, the intermediary portion may be spot welded or crimped to the patient- and doctor-sides of the guidewire. It is also possible to construct the guidewire as one continual spring but alter the structure or other characteristic of the intermediary portion of the guidewire post-manufacture (e.g., by inelastically stretching the guidewire where the intermediary portion is to be or by omitting the core wire from the guidewire (but leaving the spring wire) at the location where the intermediary portion is to be).

Figure 13C:
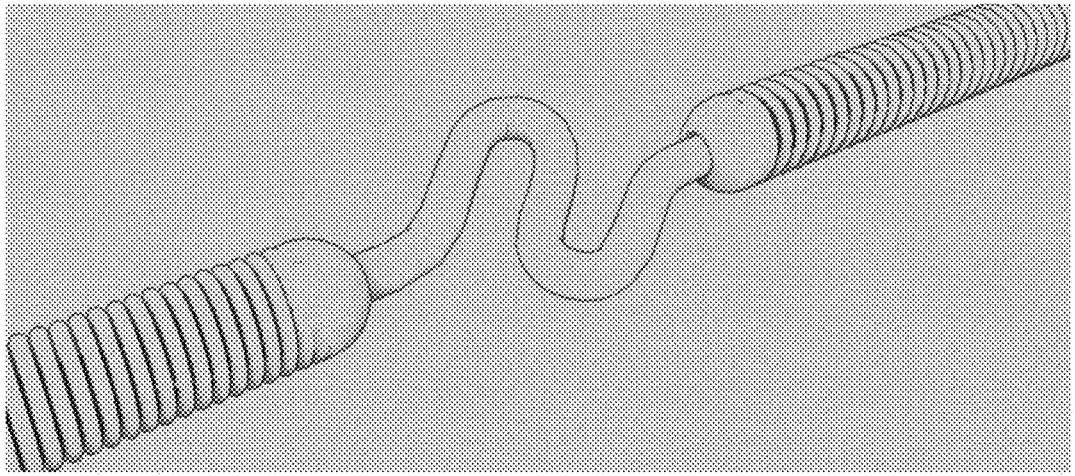
FIGS. 13C and 13D are first and second expanded views of a flat intermediary portion of a eleventh exemplary guidewire having a twisted wire configuration on both sides (where two different shading models were used to accentuate various aspects of the obstruction portion's construction)
Figure 13D:
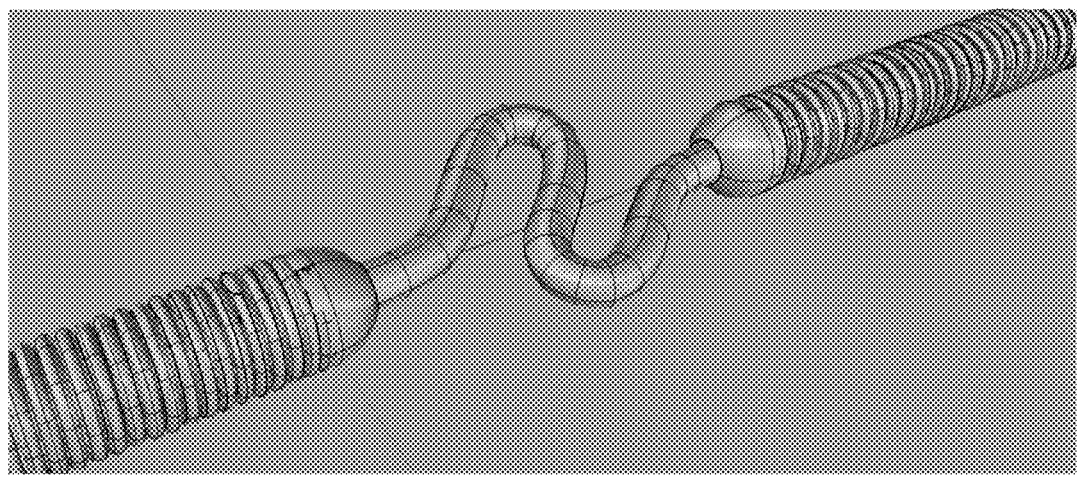

In yet another embodiment, an intermediary portion is constructed as an obstruction portion and using a material with a "spring memory" such that the intermediary portion does hold a particular shape on its own when no force is applied to it. However, when both sides of the intermediary portion are pulled away from each other the shape (e.g., an S-shape) of the material "flattens out" so that the needle can be passed over the material. Moreover, when the pulling forces are removed the intermediary portion returns essentially to its original shape. Such "spring memory" materials include, but are not limited to, metals (including memory metals such as nickel titanium ("Nitinol")) and other molded materials (such as certain plastics). In one embodiment (e.g., as shown in FIGS. 13C and 13D), the intermediary portion is S-shaped and implemented using nickel titanium wire thinner than the diameter of the patient-side portion of the guidewire (e.g., a wire having a thickness of 0.008-0.012 inches) that extends about 0.1-0.25 in in the direction of the patient- and doctor-side portions (e.g., from bonding point to bonding point) in its normal state. The normal diameter of an exemplary 0.008 inch thick S-shaped portion is preferably about 0.14 in long when the S-shape is in its normal state, and the flattened or reduced diameter of the S-shaped portion is preferably about 0.07 in long when the S-shape is in its flattened or reduced state (when no pulling force is applied). The obstruction portion generally can be a spring-like material (e.g., a metal (including a memory metal) or an elastomer) and may be of an extruded, drawn, die-cut or molded material/shape that is either solid or hollow.

In yet another embodiment, the intermediary portion is a material that has an initial shape but that shape permanently deforms after one or more "flattening outs" of the material (i.e., when both sides of the intermediary portion are pulled away from each other). In such a configuration, the shape (e.g., an S-shape) of the material "flattens out" so that the needle can be passed over the material but after one or more "flattening outs" the intermediary portion no longer returns to essentially its original shape when the pulling forces are removed.

Figure 13E:
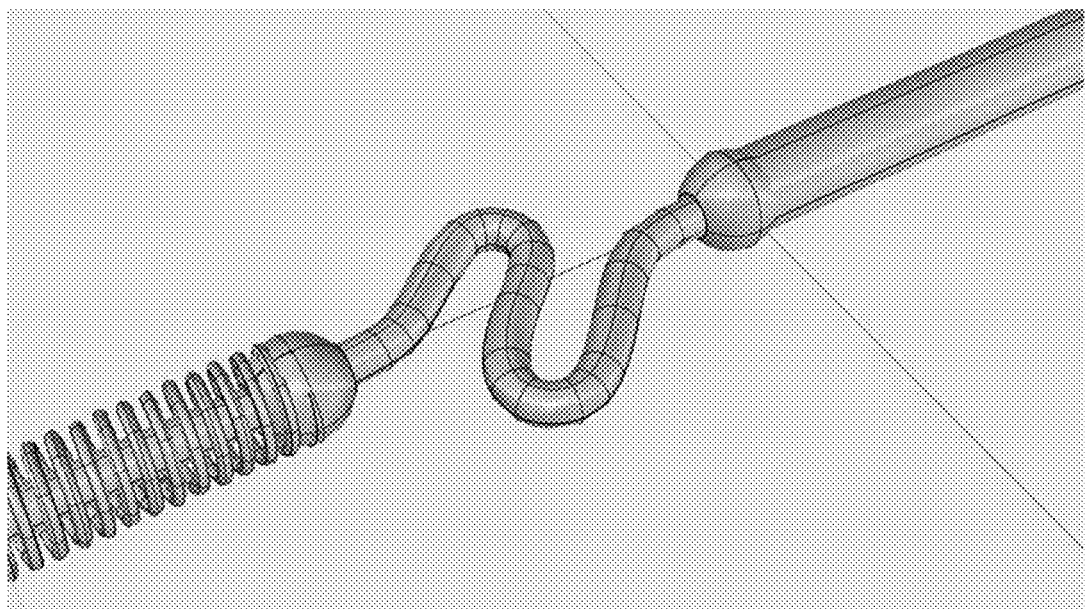
FIGS. 13E and 13F are third and fourth expanded views of a flat intermediary portion of a eleventh exemplary guidewire having a twisted wire configuration on a patient side and a straight wire configuration on a doctor-side (where two different shading models were used to accentuate various aspects of the obstruction portion's construction)
Figure 13F:
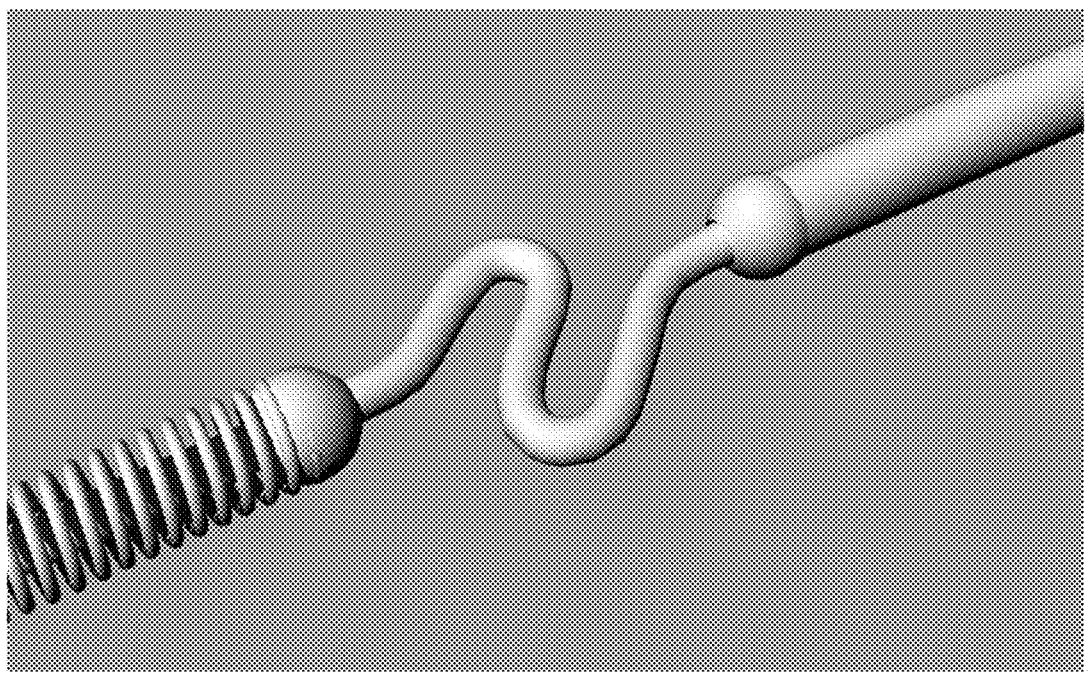

As shown in FIGS. 13E and 13F, the patient-side and doctor-side need not have the same construction. In FIGS. 13E and 13F, the patient-side (shown on the left) is constructed similar to a conventional guidewire with a coil structure (e.g., with or without an internal wire inside the coil structure). However, on the doctor-side, as it does not enter the patient's body and is only used to guide the catheter (or another enlarging needle), the doctor-side can utilize a different structure (e.g., a single wire). Thus, although the doctor-side may have the same structure as the patient-side (e.g., as far as wire thickness, windings, materials, etc.), it need not. Other exemplary structures on the doctor-side that are different than the patient-side include single-strand wire (as shown in FIGS. 13E and 13F) and multi-strand wire. Furthermore, the colors of the patient-side and doctor-side can be different for easier visual differentiation. As discussed above, the materials on the patient-side and doctor-side need not be the same either and could, instead, be different metals, fibers, plastics, elastomers or synthetic materials as long as the doctor-side is longer in length than the catheter allowing an exposed end to grip onto when the catheter needs to be advanced over the obstruction portion.

Figure 13G:
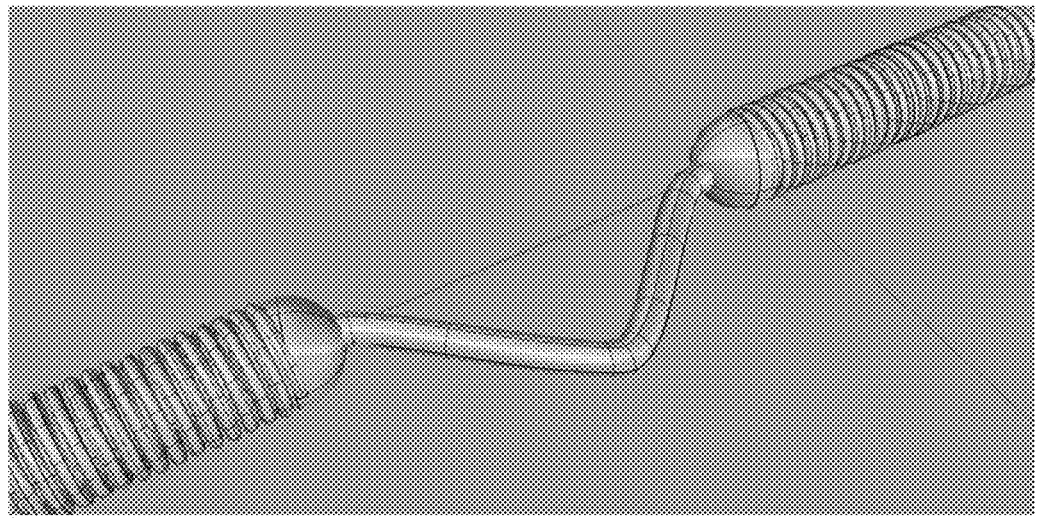
FIGS. 13G and 13H are expanded views of flat, mono-triangular and bi-triangular intermediary portions, respectively, of additional exemplary guidewires.
Figure 13H:
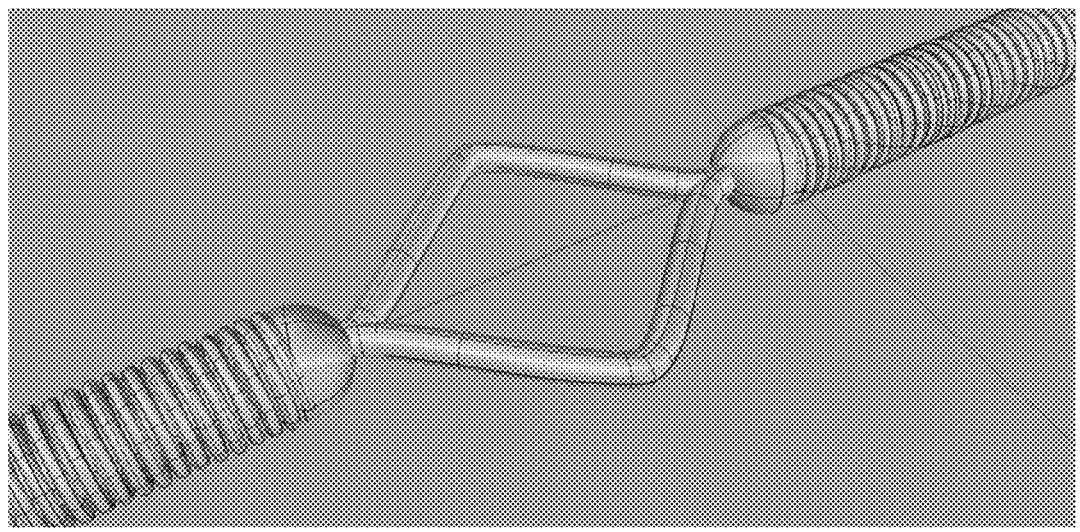
Figure 13I:
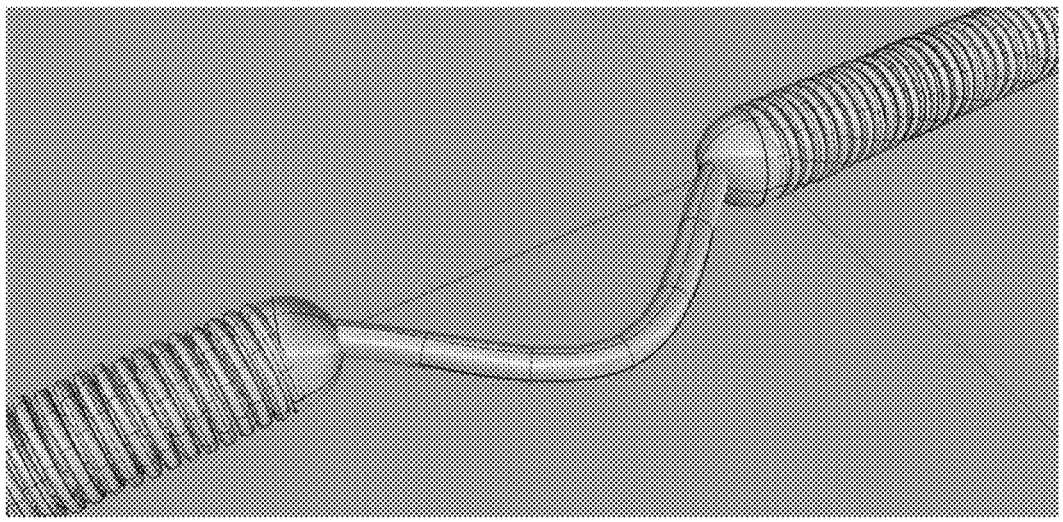
FIGS. 13I and 13J are expanded views of flat, mono-hump and bi-hump intermediary portions, respectively, of additional exemplary guidewires.
Figure 13J:
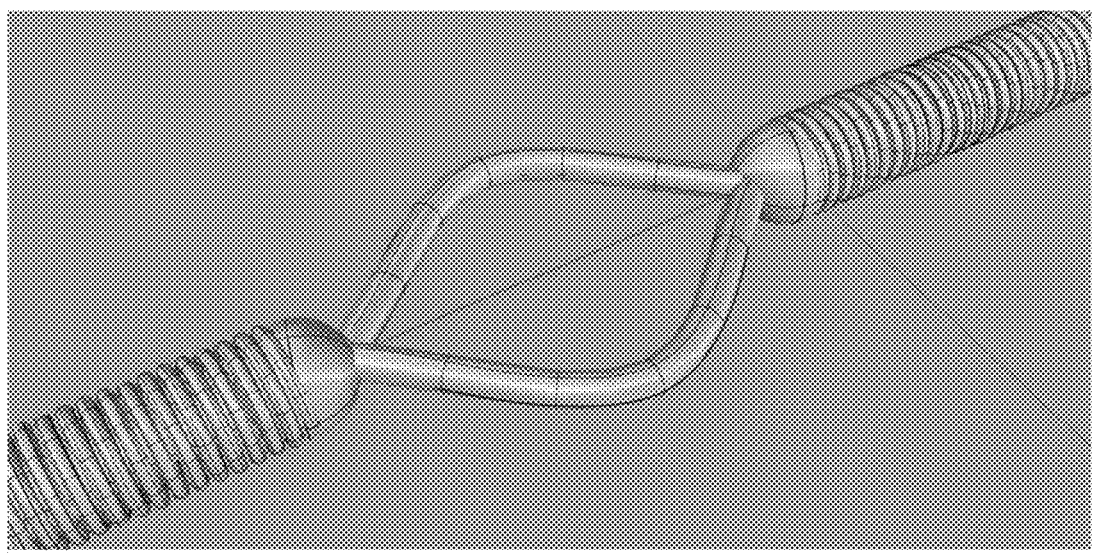

As shown in FIGS. 13G and 13H and in FIGS. 13I and 13J, an obstruction portion can be constructed from one or more spring-like segments connected between the doctor-side portion and the patient-side portion. In FIGS. 13G and 12I, the intermediary portions are mono-triangular and mono-hump shaped. However, in embodiments where there is more than one spring-like segment, the same spring-like segment shape can be duplicated in an opposite direction from another similarly shaped segment. For example, as shown in FIG. 13H, two triangular spring-like shapes face away from each other and are connected between the doctor-side portion and the patient-side portion. Similarly, as shown in FIG. 13J, two spring-like hump-shapes face away from each other and are connected between the doctor-side portion and the patient-side portion. However, as would be understood by those of skill in the art, in embodiments where there is more than one spring-like segment, the different spring-like segment shape can be configured in opposite directions from each other (e.g., a triangular shaped segment can be paired with a hump shaped segment).

Figure 13K:
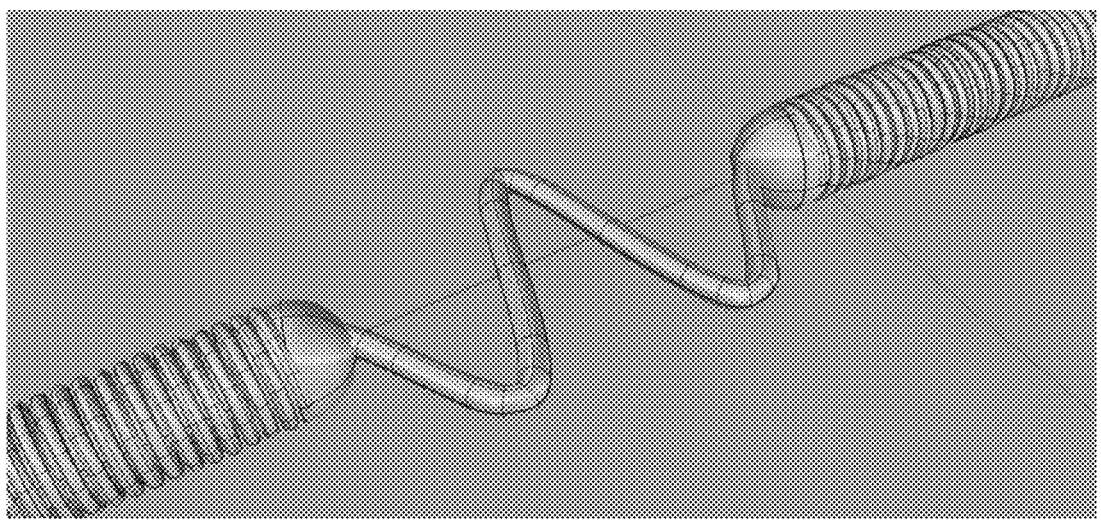
FIG. 13K is an expanded view of a flat, multi-legged intermediary portion of an additional exemplary guidewire.

Furthermore, as shown in FIG. 13K, multi-legged intermediary portions can be used that have diameters in their normal states that are larger than the diameter of the needle that the guide wire is being pushed into. Such multi-legged intermediary portions can be flat (as shown) or multi-directional (e.g., at least one of the legs of the multi-legged intermediary portion being at an angle in the x-z plane compared to another leg in the x-y plane).

In a number of the embodiments disclosed here, when the obstruction portion is a wire, the wire may be a separate material with a different diameter than one or both ends and welded to the other ends, but it does not have to be. The inner core of the left (patient) side (or the right doctor-side) could be one long length that has the portion of the mid-section altered to meet the needs for the mid-section.

While the interposed structures shown in FIGS. 13C-13K are shown as generally lying within a single plane, the interposed structures can be constructed to be non-planar to make it even more difficult to inadvertently push the intermediary portion into the needle (in the direction of the patient's body). Moreover, the interposed structure can comprise multiple segments such that the segments are generally perpendicular to each other creating a multi-directional interposed structure (e.g., one or more segments in an x-y plane and one or more segments in an x-z plane). For example, at least one additional hump-shaped segment for FIG. 13J can be added in the x-z plane compared to the existing two hump-shaped segments in the illustrated x-y plane.

Among the advantages of a number of the embodiments described above, a first noteworthy advantage is that the locations of the obstruction portion and/or the intermediary portion allow a doctor inserting the guidewire to know the proper depth to advance the guidewire. Currently, more uncertainty exists on the part of the doctor. Furthermore, the locations of the obstruction portion and/or the intermediary portion prevent the doctor from putting too much of the guidewire into the patient such that there is an insufficient amount of guidewire to stick out of the back of the catheter once it is inserted.

Figure 14A:
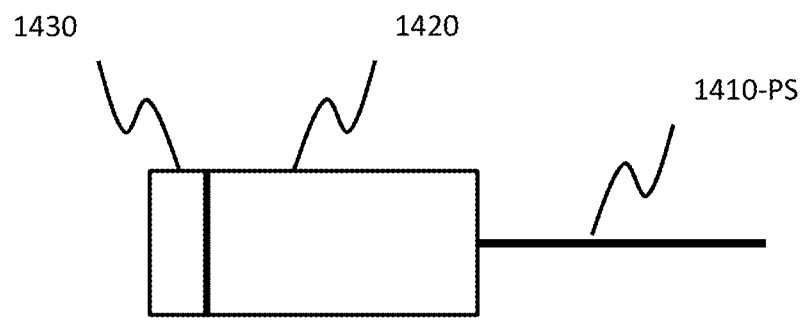
FIG. 14A is a block diagram of the general structure of a detachable guidewire where a patient side portion of the guidewire is connected to an obstruction portion or intermediary portion including a coupling or mating portion.
Figure 14B:
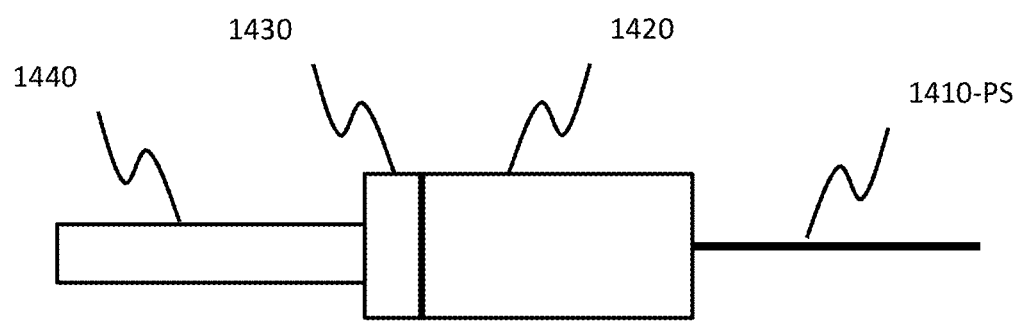
FIG. 14B is a block diagram of the general structure of a detachable guidewire of FIG. 14A in which the coupling or mating portion of the obstruction portion or intermediary portion is connected post-manufacture to a tool for manipulating the obstruction portion or intermediary portion (e.g., for reducing the diameter of an obstruction portion)
Figure 14C:
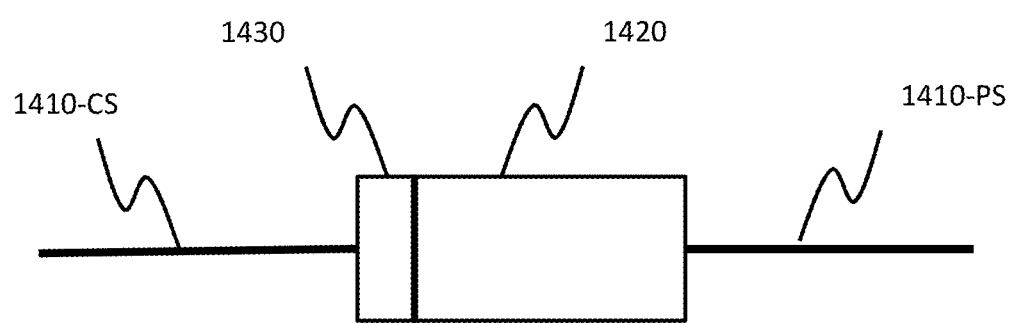
FIG. 14C is a block diagram of the general structure of a detachable guidewire of FIG. 14A in which the coupling or mating portion of the obstruction portion or intermediary portion is connected post-manufacture to a doctor-side guidewire.

In addition to integrated guidewires as discussed above, detachable guidewires are also possible based on the teachings herein. For example, rather than an integrally formed guidewire extending from the obstruction portion or intermediary portion toward the doctor, as shown in FIG. 14A, the obstruction portion and/or the intermediary portion (collectively referenced as 1420) may be fitted with a coupling or mating portion (collectively referenced as 1430) on the doctor-side of the obstruction portion and/or the intermediary portion 1420 which is connected to a patient side guidewire 1410-PS (as described with respect to the integrated guidewire). The coupling or mating portion 1430 may, after the time of manufacture, be connected to a tool 1440 (as shown in FIG. 14B) or a doctor-side guidewire 1410-CS (as shown in FIG. 14C). For example, a tool 1440 for manipulating the obstruction portions of FIGS. 10A-11D may be connected (e.g., magnetically or using a friction fit or a screw-in structure) to the coupling or mating portion 1430 and the diameter of the obstruction portion manipulated using the tool (e.g., by pushing or pulling a plunger).

When using such a tool 1440, after the patient side guidewire 1410-PS has been run through the needle and into the patient, the tool 1440 is connected to the coupling or mating portion 1430 so that the diameter of the obstruction portion can be temporarily reduced. The needle then may be passed over the obstruction portion after which the tool is detached from the coupling or mating portion 1430. The needle can then be removed from the tool 1440 and the catheter placed over the end of the tool which is then reattached to the coupling or mating portion 1430. The tool 1440 then reduces the diameter of the obstruction portion so that the catheter can pass over obstruction portion before the tool is removed. The guidewire can then be removed from the patient.

Figure 15A:
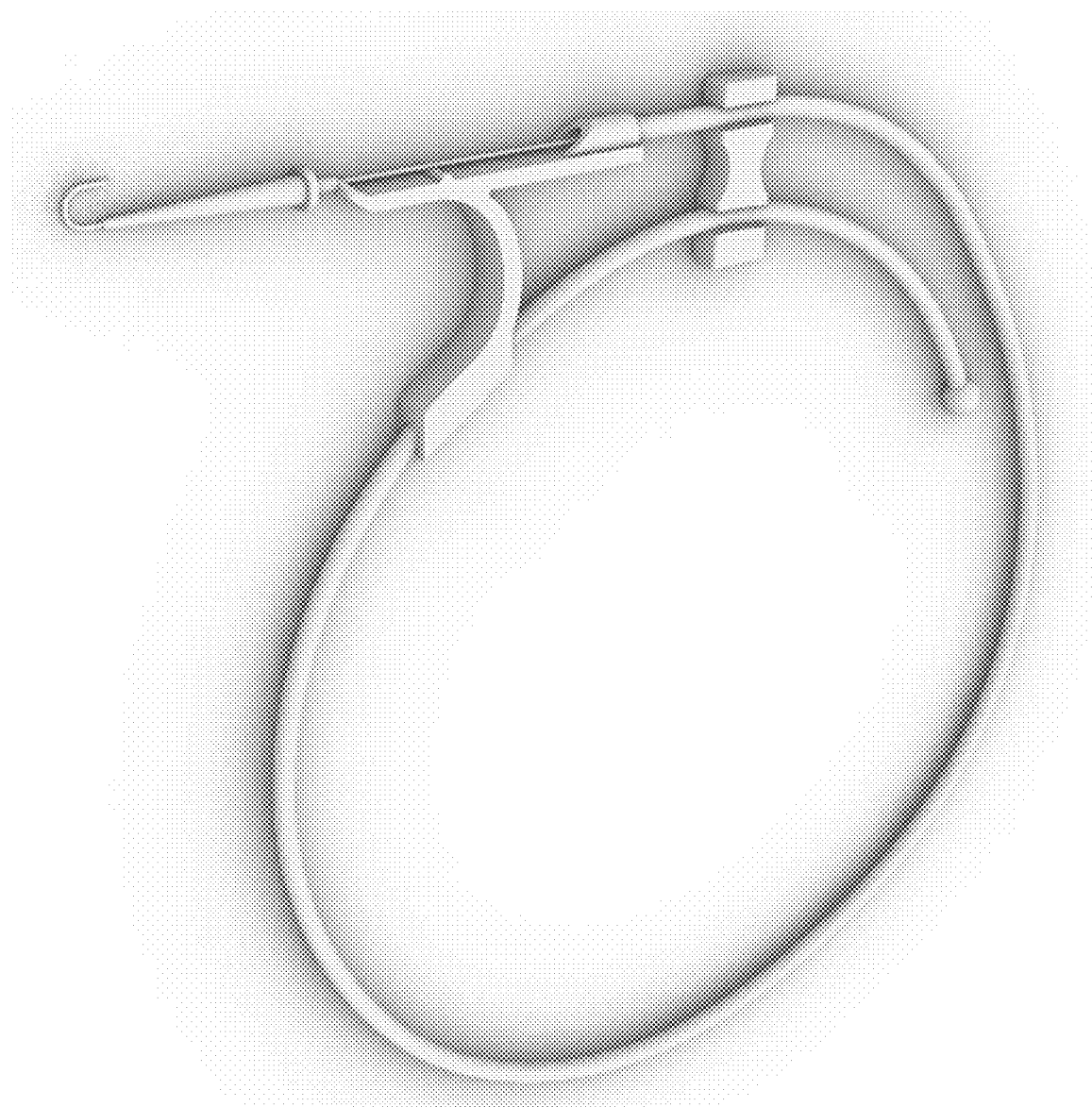
FIG. 15A is a schematic illustration of a known guidewire being held in a known guidewire dispenser prior to straightening and inserting the "J-hook" end of the guidewire into the needle of a patient.
Figure 15B:
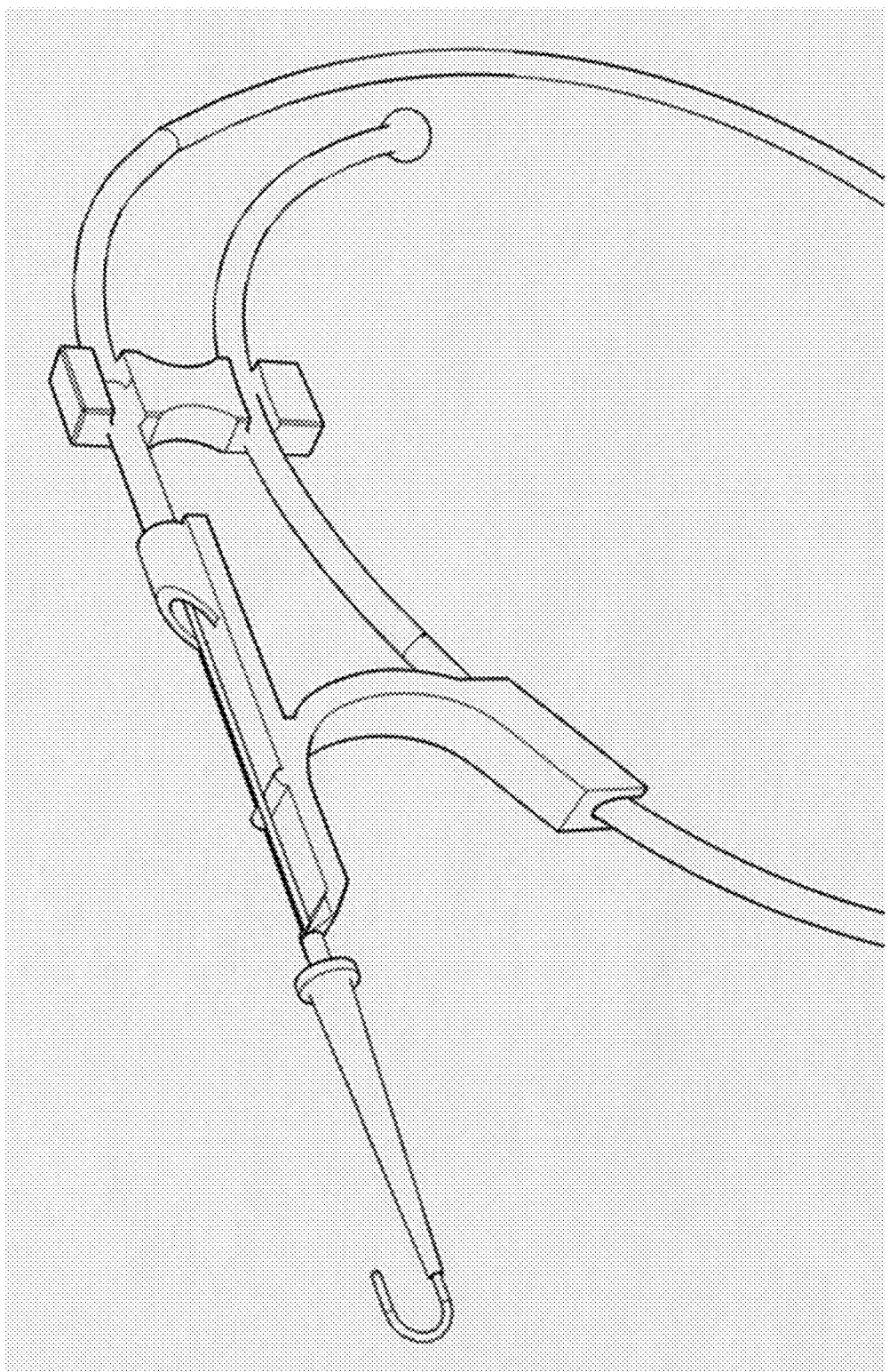
FIG. 15B is an enlarged view of the guidewire and guidewire dispenser of FIG. 15A.
Figure 15C:
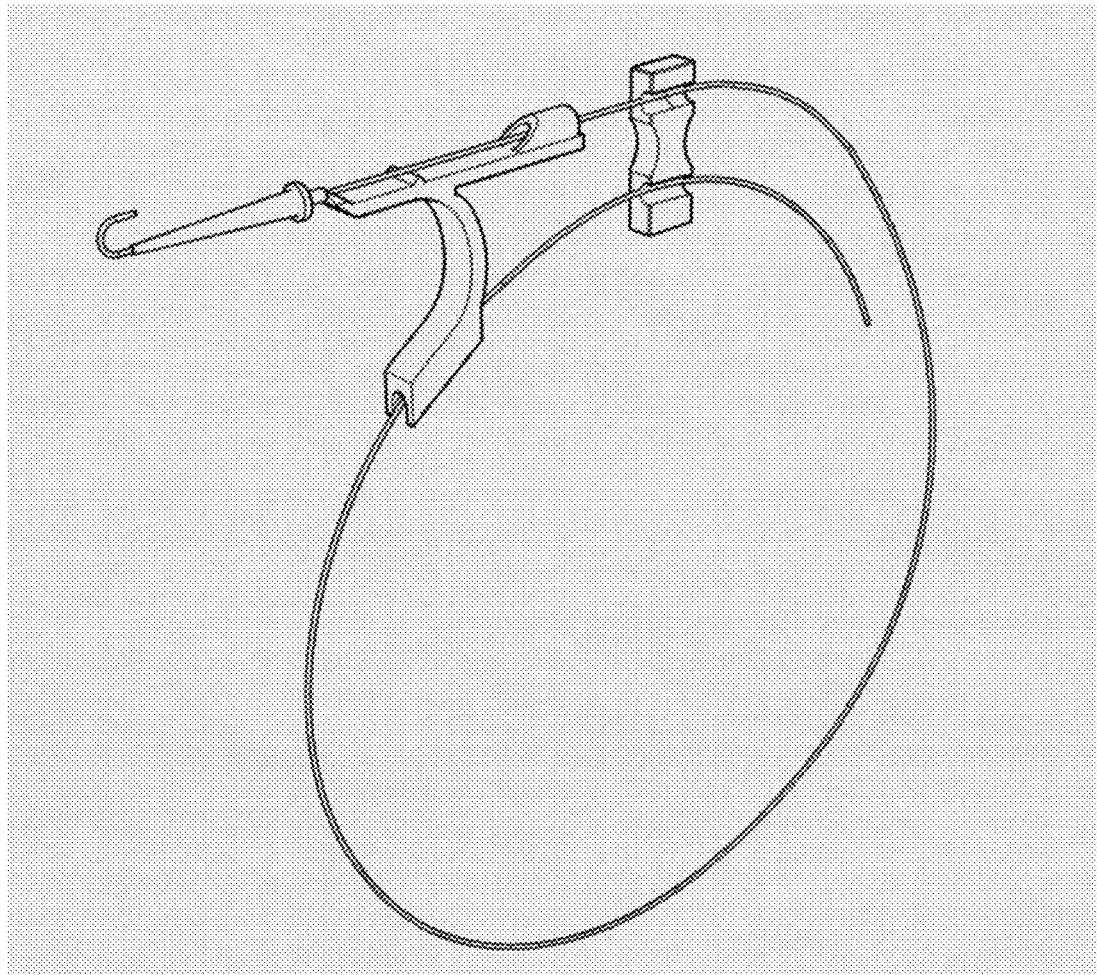
FIG. 15C is a schematic illustration of a known guidewire being held in a guidewire dispenser (that has had its plastic tubing removed for illustrative purposes) prior to straightening and inserting the "J-hook" end of the guidewire into the needle of a patient.

FIGS. 15A and 15B are a schematic illustration and a corresponding enlarged view of the schematic illustration of FIG. 15A, respectively, of a known guidewire being held in a known guidewire dispenser prior to straightening and inserting the "J-hook" end of the guidewire into the needle of a patient. The guidewire is advanced into the needle of a patient by the doctor using a thumb-pushing motion once the guidewire is inserted into the needle. In FIG. 15C, the plastic tubing surrounding the guidewire held by the guidewire dispenser has been removed for illustrative purposes.

Figure 16A:
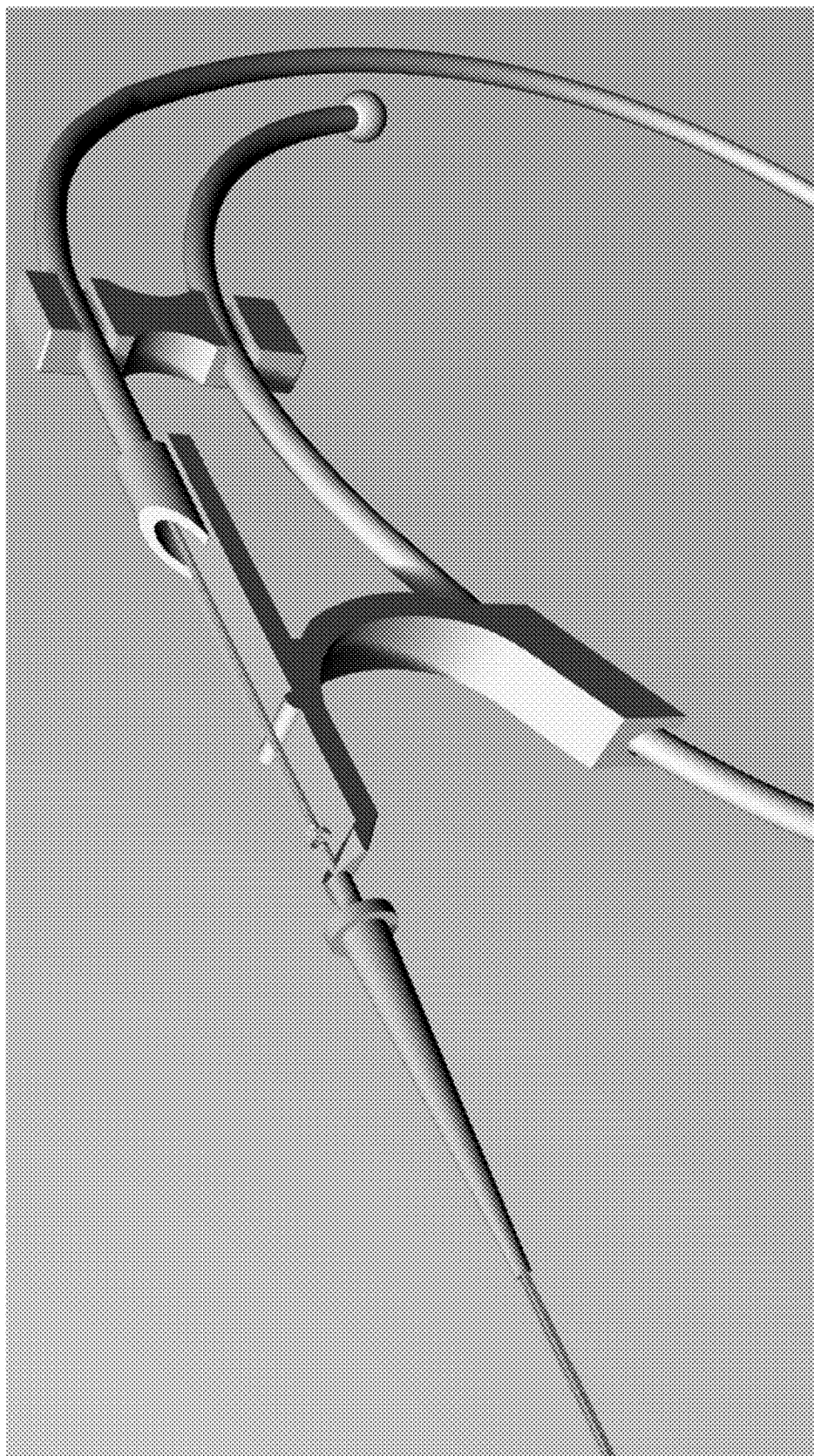
FIG. 16A is a schematic illustration of a guidewire having a first obstruction portion being held in a guidewire dispenser (having a tubing, such as a plastic tubing) where the guidewire has been inserted into the needle of a patient (and therefore into the patient) substantially up to the obstruction portion.
Figure 16B:
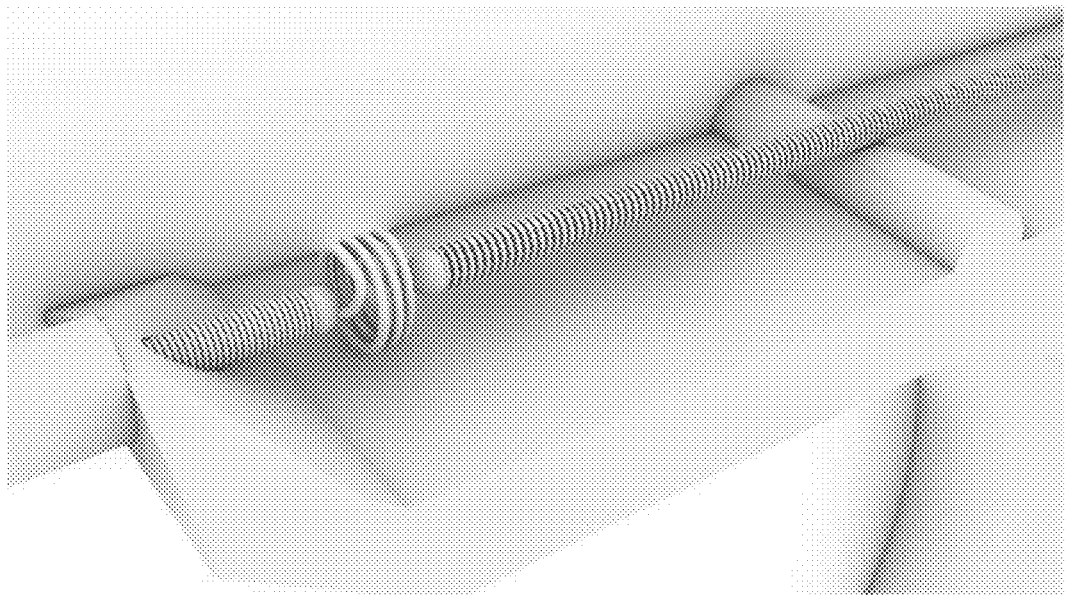
FIG. 16B is an enlarged view of the guidewire dispenser of FIG. 16A where the guidewire has been inserted into the needle of a patient (and therefore into the patient) substantially up to the obstruction portion.
Figure 16C:
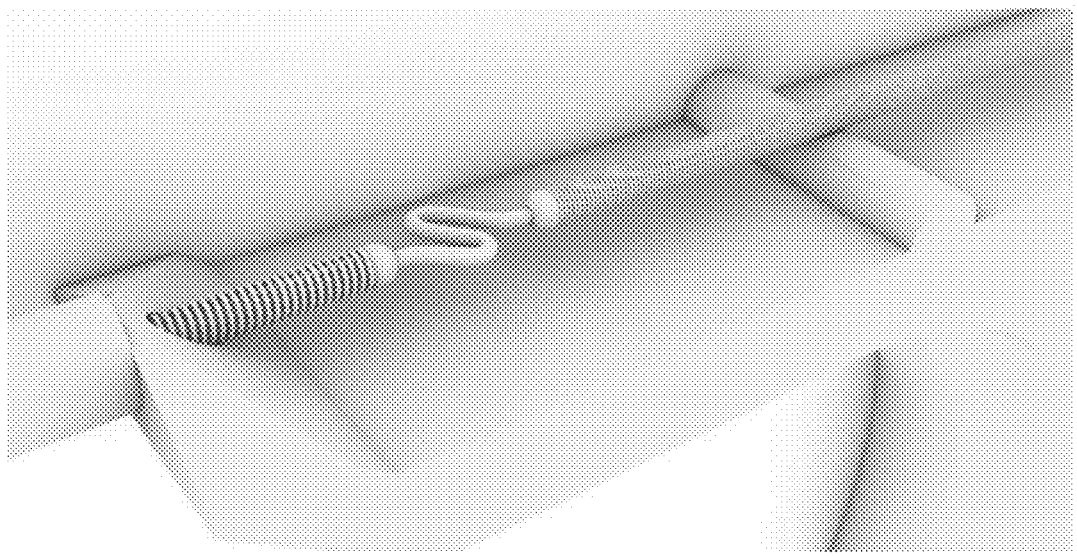
FIG. 16C is a schematic illustration of a guidewire having a second obstruction portion being held in a guidewire dispenser where the guidewire has been inserted into the needle of a patient (and therefore into the patient) substantially up to the obstruction portion.
Figure 16D:
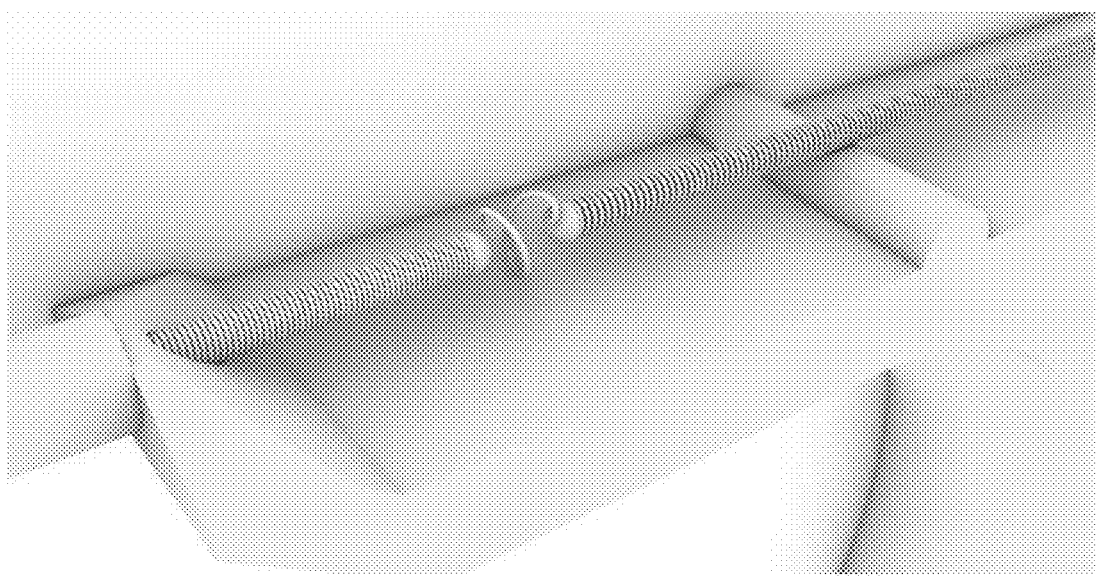
FIG. 16D is a schematic illustration of a guidewire having a third obstruction portion being held in a guidewire dispenser where the guidewire has been inserted into the needle of a patient (and therefore into the patient) substantially up to the obstruction portion.

FIG. 16A is a schematic illustration of a guidewire having a first obstruction portion (although any of the other obstruction portions described herein could have been used) being held in a guidewire dispenser (having a tubing surrounding a portion of the guidewire) so that the guidewire can be inserted into the needle of a patient (and therefore into the patient) only substantially up to the obstruction portion. FIG. 16B shows an enlarged illustration of the configuration of FIG. 16A where the guidewire is at the furthest point it can be pushed through the dispenser. At this point, the doctor will need to slightly pull back on the dispenser—grab the guidewire just to the left of the tip of the dispenser (and to the right or the needle) and hold the guidewire as the dispenser is pulled to the right pulling out the remainder of the guidewire. This process guarantees the obstruction portion never gets into the needle and into the body. FIGS. 16C and 16D are schematic illustrations of a guidewire having a second and a third obstruction portion (although any of the other obstruction portions described herein could have been used) being held in a guidewire dispenser where the guidewire has been inserted into the needle of a patient (and therefore into the patient) and advanced to substantially its furthest forward position it can go in the dispenser.

In a first embodiment, the diameter of the tubing is larger than the diameter of the obstruction portion in its non-reduced diameter state so that the guidewire passes through the tubing without continuous friction between the obstruction portion and the tubing. In another embodiment, a portion of the tubing and/or a portion of the advancing platform of the dispenser has a diameter that is the same as or is smaller than the diameter of the obstruction portion in its non-reduced diameter state such that the doctor is provided tactile feedback that the obstruction portion is approaching or has arrived at the advancing platform without the doctor having to frequently look down at the dispenser.

Figure 17:
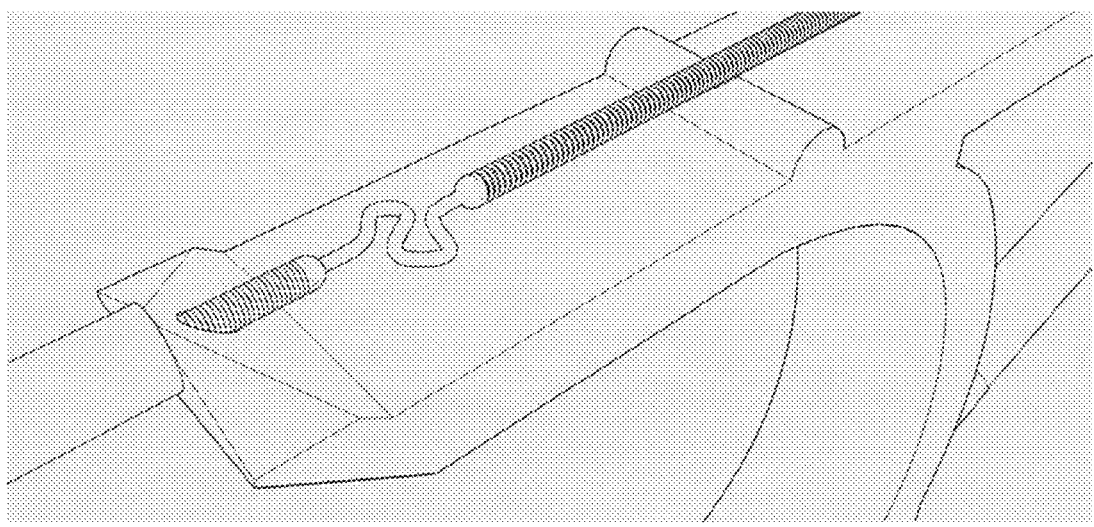
FIG. 17 is a schematic illustration of a guidewire having a non-rigid portion acting as an intermediary portion (such as one of the flimsy-cord intermediary portions described herein) being held in a guidewire dispenser where the guidewire has been inserted into the needle of a patient (and therefore into the patient) substantially up to the non-rigid portion.

Similarly, FIG. 17 is a schematic illustration of a guidewire having an intermediary portion (such as one of the intermediary portions described herein) being held in a guidewire dispenser where the guidewire has been inserted into the needle of a patient (and therefore into the patient) almost substantially up to the intermediary portion. The length of the intermediary portion need not be of the scale shown and indeed may be longer or shorter. An advantage with the illustrated intermediary portion is that it cannot be easily advanced by the movement of the doctor's thumb because it is non-rigid (i.e., it lacks the rigidity of the portion of guidewire that has been inserted into the patient). However, by holding or pinching the guidewire at the location between the dispenser and the needle, the dispenser can be pulled off of the doctor-side of the guidewire, thereby exposing the proper length of the guidewire that is to be inserted into the catheter.

While certain configurations of structures have been illustrated for the purposes of presenting the basic structures of the present invention, one of ordinary skill in the art will appreciate that other variations are possible which would still fall within the scope of the appended claims. For example, the intermediary portion need not be substantially half way between the distal ends of the doctor- and patient-side portions. The intermediary portion or obstruction portion need only be positioned such that a doctor can put the catheter over the doctor-side portion and the wire extends outside the back of the catheter before the leading tip of the catheter reaches the obstruction portion. In one such embodiment, the patient-side portion is substantially longer than the doctor-side portion (e.g., 40 cm vs. 15 cm). In an alternate embodiment, the patient-side portion is shorter than the doctor-side.

The invention claimed is:

1. A guidewire for insertion into a needle during a medical procedure, the guidewire comprising:
 a patient-side portion having a first diameter less than an inner diameter of the needle;
 a doctor-side portion having a second diameter less than the inner diameter of the needle; and
 an intermediary portion, interposed between the patient-side portion and the doctor-side portion, having a diameter greater than the inner diameter of the needle and greater than the first diameter of the patient-side portion such that the intermediary portion does not advance into the needle during the medical procedure when a medical professional pushes axially on the doctor-side portion.

2. The guidewire as claimed in claim 1, wherein the intermediary portion comprises an obstruction portion having a reducible diameter that reduces under force exerted by a medical professional after insertion of the patient-side portion of the guidewire into the needle.

3. The guidewire as claimed in claim 2, wherein the obstruction portion has a temporarily reducible diameter.

4. The guidewire as claimed in claim 2, wherein the obstruction portion has a permanently reducible diameter.

5. The guidewire as claimed in claim 2, wherein the obstruction portion is integrated with at least one of the patient-side and doctor-side of the guidewire.

6. The guidewire as claimed in claim 1, wherein the intermediary portion is located between the patient-side portion and the doctor-side portion such that the patient-side portion and the doctor-side portion have substantially similar lengths.

7. The guidewire as claimed in claim 2, wherein the obstruction portion is affixed to at least one of the patient-side portion and the doctor-side portion.

8. The guidewire as claimed in claim 2, wherein the obstruction portion is welded to at least one of the patient-side portion and the doctor-side portion.

9. The guidewire as claimed in claim 2, wherein the obstruction portion is detachably connected to at least one of the doctor-side portion and the patient-side portion.

10. The guidewire as claimed in claim 2, wherein the obstruction portion comprises a spring memory obstruction portion having a temporarily reducible diameter.

11. The guidewire as claimed in claim 2, wherein the obstruction portion comprises a nickel titanium obstruction portion having a temporarily reducible diameter.

12. The guidewire as claimed in claim 2, wherein at least one of the doctor-side portion and the obstruction portion is colored differently than the patient-side portion.

13. A guidewire for insertion into a needle during a medical procedure, the guidewire comprising:
a patient-side portion;
a doctor-side portion; and
an intermediary portion interposed between the patient-side portion and the doctor-side portion having a material having sufficiently less rigidity in the axial direction of the guidewire than the patient-side portion such that the intermediary portion does not advance into the needle during the medical procedure when a medical professional pushes axially on the doctor-side portion.

14. The guidewire as claimed in claim 13, wherein the intermediary portion comprises a material having less rigidity than the patient-side portion and the doctor-side portion.

15. The guidewire as claimed in claim 13, wherein the intermediary portion comprises a string-like material.

16. The guidewire as claimed in claim 1, wherein the patient-side portion includes a J-hook portion at a distal end from the intermediary portion.

17. The guidewire as claimed in claim 2, wherein the obstruction portion comprises a planar spring memory obstruction portion having a temporarily reducible diameter.

18. The guidewire as claimed in claim 2, wherein the obstruction portion comprises a non-planar spring memory obstruction portion having a temporarily reducible diameter.

19. The guidewire as claimed in claim 1, wherein the first and second diameters are the same.

20. The guidewire as claimed in claim 2, wherein a non-reduced diameter of the obstruction portion is two to three times the reduced diameter.

21. The guidewire as claimed in claim 13, wherein the patient-side portion includes a J-hook portion at a distal end from the intermediary portion.

22. The guidewire as claimed in claim 2, wherein the obstruction portion is S-shaped.

23. The guidewire as claimed in claim 2, wherein the obstruction portion is a wire having a thickness that is less than the first diameter.

24. A catheter system comprising:
a needle having a first inner diameter;
a catheter having a second inner diameter; and
a guidewire for insertion into the needle and the catheter during a medical procedure, the guidewire comprising:
a patient-side portion having a first diameter less than the first inner diameter of the needle and less than the second inner diameter of the catheter;
a doctor-side portion having a second diameter less than the first inner diameter of the needle and less than the second inner diameter of the catheter; and
an intermediary portion, interposed between the patient-side portion and the doctor-side portion, having a diameter greater than the first inner diameter of the needle and greater than the first diameter of the patient-side portion such that the intermediary portion does not advance into the needle during the medical procedure when a medical professional pushes axially on the doctor-side portion.

25. The catheter system as claimed in claim 24, wherein the doctor-side portion of the guidewire is longer than the catheter.

26. The catheter system as claimed in claim 24, wherein the intermediary portion comprises an obstruction portion having a reducible diameter that reduces under force exerted by a medical professional after insertion of the patient-side portion of the guidewire into the needle.

27. The catheter system as claimed in claim 26, wherein the obstruction portion has a temporarily reducible diameter.

28. The catheter system as claimed in claim 26, wherein the obstruction portion comprises a spring memory obstruction portion having a temporarily reducible diameter.

29. The catheter system as claimed in claim 28, wherein a non-reduced diameter is two to three times the temporarily reduced diameter.

30. The guidewire as claimed in claim 1, wherein the intermediary portion comprises means for obstructing the guidewire from advancing into the needle during the medical procedure when the medical professional pushes axially on the doctor-side portion.

31. The guidewire as claimed in claim 13, wherein the intermediary portion comprises means for non-rigidly preventing the guidewire from advancing into the needle during the medical procedure when the medical professional pushes axially on the doctor-side portion.

32. The catheter system as claimed in claim 24, wherein the intermediary portion comprises means for obstructing the guidewire from advancing into the needle during the medical procedure when the medical professional pushes axially on the doctor-side portion.

33. A catheter system comprising:
a needle having a first inner diameter;
a catheter having a second inner diameter; and
a guidewire for insertion into the needle and the catheter during a medical procedure, the guidewire comprising:
a patient-side portion having a first diameter less than the first inner diameter of the needle and less than the second inner diameter of the catheter;
a doctor-side portion having a second diameter less than the first inner diameter of the needle and less than the second inner diameter of the catheter; and
an intermediary portion interposed between the patient-side portion and the doctor-side portion having a material having sufficiently less rigidity in the axial direction of the guidewire than the patient-side portion such that the intermediary portion does not advance into the needle during the medical procedure when a medical professional pushes axially on the doctor-side portion.

34. The catheter system as claimed in claim 33, wherein the intermediary portion comprises means for non-rigidly preventing the guidewire from advancing into the needle during the medical procedure when the medical professional pushes axially on the doctor-side portion.

* * * * *